US009278947B2

(12) United States Patent
Rehavi et al.

(10) Patent No.: US 9,278,947 B2
(45) Date of Patent: Mar. 8, 2016

(54) SEROTONIN REUPTAKE INHIBITORS AS DRUGS HAVING PERIPHERAL-SYSTEM-RESTRICTED ACTIVITY

(71) Applicant: Ramot at Tel-Aviv University Ltd., Tel-Aviv (IL)

(72) Inventors: Moshe Rehavi, Ramat-HaSharon (IL); David Gurwitz, Hod-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 334 days.

(21) Appl. No.: 13/757,944

(22) Filed: Feb. 4, 2013

(65) Prior Publication Data

US 2013/0143960 A1    Jun. 6, 2013

Related U.S. Application Data

(63) Continuation-in-part of application No. 12/308,671, filed as application No. PCT/IL2007/000756 on Jun. 21, 2007.

(60) Provisional application No. 60/815,582, filed on Jun. 22, 2006.

(51) Int. Cl.
| | |
|---|---|
| *C07D 307/91* | (2006.01) |
| *A61K 31/343* | (2006.01) |
| *A61K 45/00* | (2006.01) |
| *A61K 45/06* | (2006.01) |
| *C07D 307/87* | (2006.01) |

(52) U.S. Cl.
CPC ............ *C07D 307/91* (2013.01); *A61K 31/343* (2013.01); *A61K 45/00* (2013.01); *A61K 45/06* (2013.01); *C07D 307/87* (2013.01)

(58) Field of Classification Search
CPC ..... C07D 307/91; A61K 31/343; A61K 45/00
USPC .......................................... 514/469; 549/467
See application file for complete search history.

(56) References Cited

U.S. PATENT DOCUMENTS

| | | | |
|---|---|---|---|
| 5,296,483 | A | 3/1994 | Bodor |
| 6,777,437 | B2 | 8/2004 | Mattson et al. |
| 6,967,259 | B2 | 11/2005 | Malik et al. |
| 2006/0293309 | A1 | 12/2006 | Thor et al. |

FOREIGN PATENT DOCUMENTS

| | | |
|---|---|---|
| CN | 1708303 | 12/2005 |
| CN | 1741803 | 3/2006 |
| WO | WO 03/026563 | 4/2003 |
| WO | WO 2004/047840 | 6/2004 |
| WO | WO 2004/064753 | 8/2004 |
| WO | WO 2006/131923 | 12/2006 |
| WO | WO 2007/148341 | 12/2007 |

OTHER PUBLICATIONS

Official Action Dated Nov. 5, 2013 From the US Patent and Trademark Office Re. U.S. Appl. No. 12/308,671.
Notification of Office Action Dated Nov. 24, 2014 From The State Intellectual Property Office of the People's Republic of China Re. Application No. 201310666405.4 and Its Summary in English.
International Preliminary Report on Patentability Dated Jan. 8, 2009 From the International Bureau of WIPO Re.: Application No. PCT/IL2007/000756.
International Search Report Dated Dec. 21, 2007 From the International Searching Authority Re.: Application No. PCT/IL2007/000756.
Written Opinion Dated Dec. 21, 2007 From the International Searching Authority Re.: Application No. PCT/IL2007/000756.
Liu "Selective Serotonin Recycling Inhibitors (SSRIs) and its application in Psychiatric Clinics", Shangdong Archives of Psychiatry, 16(4):251-253, Dec. 31, 2003. Translation of Abstract.
Yu et al. "The Clinical Application of Citalopram", Nervous diseases and Mental Health, 5(1): 75-77, Feb. 28, 2005. Translation of Abstract.
Official Action Dated Mar. 3, 2015 From the US Patent and Trademark Office Re. U.S. Appl. No. 12/308,671.
Dalgaard et al. "Metabolism and Excretion of Citalopram in Man: Identification of O-Acyl- and N-Glucoronides", Xenobiotica, 29(10): 1033-1041, 1999.
Applicant-Initiated Interview Summary Dated Mar. 31, 2014 From the US Patent and Trademark Office Re. U.S. Appl. No. 12/308,671.
Official Action Dated Apr. 22, 2013 From the US Patent and Trademark Office Re. U.S. Appl. No. 12/308,671.

*Primary Examiner* — Jennifer M Kim

(57) ABSTRACT

Serotonin reuptake inhibitor compounds which are designed to exert serotonin uptake inhibitory activity in the peripheral system while being devoid of CNS activity, and a process of preparing same are disclosed. Further disclosed are pharmaceutical compositions containing same and uses thereof in the treatment of medical conditions associated with peripheral serotonin levels and/or activity, and/or platelet aggregation.

7 Claims, 8 Drawing Sheets

(7 of 8 Drawing Sheet(s) Filed in Color)

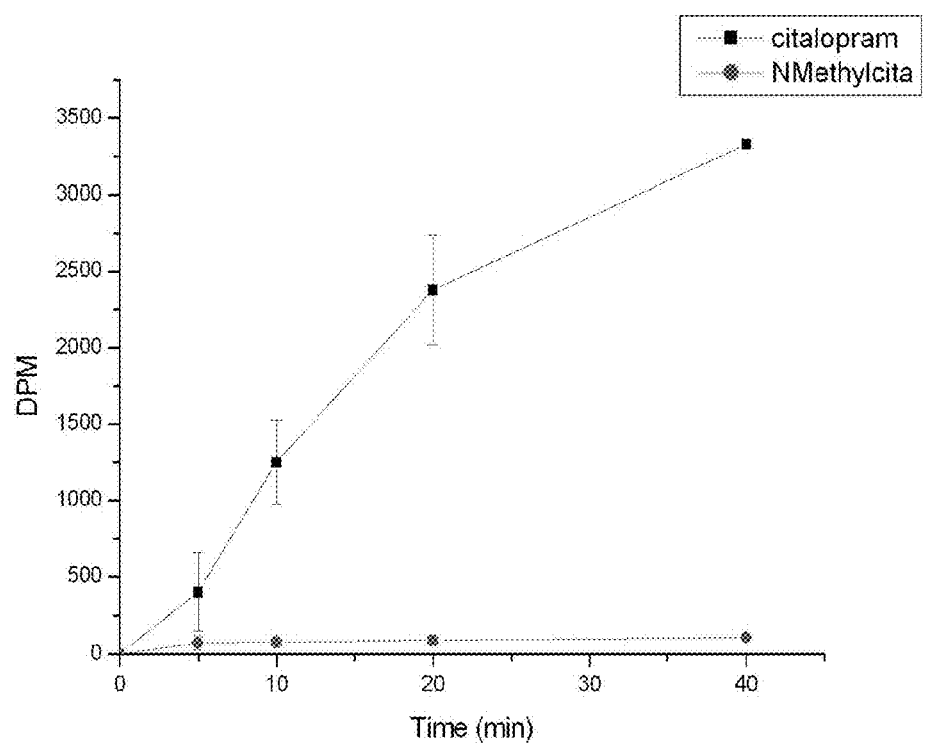

SEROTONIN REUPTAKE INHIBITORS AS DRUGS HAVING PERIPHERAL-SYSTEM-RESTRICTED ACTIVITY

RELATED APPLICATIONS

This application is a continuation-in-part (CIP) of U.S. patent application Ser. No. 12/308,671 filed on Jun. 29, 2010, which is a National Phase of PCT Patent Application No. PCT/IL2007/000756 filed on Jun. 21, 2007, which claims the benefit of priority under 35 USC §119(e) of U.S. Provisional Patent Application No. 60/815,582 filed on Jun. 22, 2006. The contents of the above applications are all incorporated by reference as if fully set forth herein in their entirety.

FIELD AND BACKGROUND OF THE INVENTION

The present invention relates to novel therapeutically active compounds and more particularly, to novel serotonin reuptake inhibitors (SRI) and their use as therapeutic agents for treating platelet-aggregation associated diseases and disorders, as well as other peripheral medical conditions.

Acute myocardial infarction (AMI or MI), also known as a heart attack, is a disorder that occurs when the blood supply to a part of the heart is interrupted, and the resulting ischemia (shortage in oxygen) causes damage and potential death of heart tissue. Currently MI is the leading cause of death for both men and women all over the world, causing 12.6% of deaths worldwide (a higher mortality rate than cancer). According to the World Health Organization reports, rates of MI-related death are much higher in countries with higher life expectancies, and keep increasing as better treatments become available for common cancers such as colon and breast cancers. Some of the main risk factors are a previous history of vascular disease such as atherosclerotic coronary heart disease and/or angina, a previous heart attack or stroke, any previous episode of abnormal heart rhythms or syncope, age (men over 40 and women over 50), smoking, excessive alcohol consumption, the abuse of certain illicit drugs, high triglyceride levels, high LDL and low HDL, diabetes, high blood pressure, obesity, and chronically high levels of mental stress.

The risk of a new or recurrent myocardial infarction decreases with strict blood pressure management and lifestyle changes, primarily smoking cessation, regular exercise, a sensible diet for patients with heart disease, and limitation of alcohol intake. Patients whom experienced a coronary event are typically prescribed several chronic medications with the aim of preventing secondary cardiovascular events such as further myocardial infarctions, congestive heart failure or cerebrovascular accident (CVA). Such medications include anti-platelet drugs such as aspirin and/or clopidogrel (Plavix) which reduce the risk of plaque rupture and recurrent myocardial infarction.

Ischemic heart disease or coronary artery disease (CAD), stroke, or pulmonary embolism, are all diseases that share the phenomena of spontaneous formation of small blood clots, unrelated to injury of blood vessels and initiated by aggregation of blood platelets inside intact blood vessels. These small platelet aggregates are carried in the blood stream until they reach small capillaries, where they might cause local ischemia by blocking small capillaries in the heart, lungs or brain tissues. Such tiny clots are also implicated in the blockade of blood vessels in the legs, a common complication of diabetes. Hence, drugs that can treat ischemia can be used beneficially to treat medical conditions which include ischemic heart disease (IHD), myocardial infarction (MI), cerebral stroke, pulmonary embolism, and type-2 diabetes-associated vascular abnormalities.

Aspirin, introduced in the late $19^{th}$ century by Bayer (Germany), is the first synthetic drug ever marketed as a pain-relief and anti-inflammatory drug. In the second half of the $20^{th}$ century aspirin has been shown to act by inhibiting the activity of cyclooxygenase enzymes, a key step in the synthesis of prostaglandins, endogenous mediators of pain and inflammation. It was realized that since prostaglandins play a key role in the increased platelet aggregation associated with inflammation, aspirin can act as a potent anti-platelet agent when given chronically, and therefore can protect from diseases such as CAD, MI, stroke and pulmonary embolism. Thus, aspirin has become the most widely prescribed drug globally, and is given as preventive treatment in CAD [1, 2]. Aspirin is also prescribed as preventive treatment against cardiovascular complications in type-2 diabetes [3].

However, blocking prostaglandins production by aspirin cannot fully protect individuals from increased platelet aggregation, mainly since it has been found that additional endogenous modulators (such as, for example, thrombin and adenosine) are implicated in platelet aggregation during inflammation. Moreover, aspirin is contra-indicated in individuals with ulcers, gastritis, ulcerative colitis, due to its tendency to increase gastrointestinal bleeding. Therefore, there is clinical validity to develop additional anti-platelet drugs, as add-on therapy for individuals who receive chronic aspirin, or as replacement for aspirin in individuals in whom aspirin is contra-indicated.

Clopidogrel causes irreversible inhibition of the adenosine diphosphate (ADP) receptor (P2Y12) on platelet cell membranes, which is a key participant in the process of platelet aggregation. The obturation of this receptor inhibits platelet aggregation by blocking activation of the glycoprotein IIb/IIIa pathway. Clopidogrel is indicated for prophylactic prevention of vascular ischaemic events in patients with symptomatic atherosclerosis, in cases of acute coronary syndrome without ST-segment (the part of an electrocardiogram immediately following the QRS complex and merging into the T wave) elevation (NSTEMI) along with aspirin, and for the prevention of thromboembolism after placement of intracoronary stent also along with aspirin. The use of clopidogrel over aspirin is recommended for patients with a history of gastric ulceration requiring anti-platelet therapy. However, a recent study has shown that patients with healed aspirin-induced ulcers receiving aspirin plus the proton pump inhibitor esomeprazole had a lower incidence of recurrent ulcer bleeding than patients receiving clopidogrel. Additionally, antithrombotic doses of clopidogrel were found to have limited effects on bleeding and standard measures of platelet aggregation [4]. Furthermore, clopidogrel is associated with other serious adverse effects which include severe neutropenia, thrombotic thrombocytopenic purpura, hemorrhage which is aggravated by the co-administration of aspirin, gastrointestinal hemorrhage, cerebral hemorrhage and erectile dysfunction.

Serotonin (5-HT) is a major central nervous system (CNS) monoamine neurotransmitter, which is synthesized in serotonergic neurons in the CNS (about 10%) and enterochromaffin (EC) cells (Kulchitsky cells) in the gastrointestinal tract of animals (about 90%). Serotonin is also found in many mushrooms and plants. Serotonin is stored outside the brain mostly in platelets of the blood stream. Serotonin was first isolated and named in 1948 by Rapport, Green and Page, who identified it initially as a vasoconstrictor substance in blood serum—hence serotonin, a serum agent affecting vascular tone. Rapport and co-workers also identified serotonin chemically as 5-hydroxytryptamine (5-HT), and since then it was studied and found to exhibit a wide range of physiological roles.

Most of 5-HT is synthesized by tryptophan hydroxylase-1 (TPH1), which is expressed almost exclusively in the enterochromaffin cells of the gastrointestinal tract. 5-HT is secreted into the blood and taken up by the 5-HT transporter (5-HTT) primarily into platelets, which are the richest reservoir of 5-HT in the periphery. In the blood, 5-HT is stored almost exclusively in the dense granules of platelets and is almost absent in the plasma. Notably, blood lymphocytes (both B and T lymphocytes) also express functional 5-HTT and can accumulate 5-HT. However, the capacity of lymphocytes to store and to release 5-HT has not been proven to date; the lymphocyte reservoir is apparently smaller compared with the large platelets 5-HT storage capacity.

As a CNS active substance, serotonin plays an important role in the regulation of aggression, mood, body temperature, sleep, vomiting, sexual drive and appetite. Low levels thereof or low bioavailability are associated with several disorders such as increased aggressive and angry behaviors, clinical depression, obsessive-compulsive disorder (OCD), migraine, irritable bowel syndrome (IBS), tinnitus, fibromyalgia (FM or FMS), bipolar disorder, anxiety disorders and intense religious experiences. In addition, abnormal serotonergic neurons have been associated with the risk of sudden infant death syndrome (SIDS). When taken orally, 5-HT does not pass into the serotonergic pathways of the CNS because it cannot cross the blood-brain barrier (BBB).

In addition to its CNS activities, 5-HT is involved in several peripheral activities; these include cardiovascular modulating effects (both vasoconstrictor and vasodilator), potent prothrombotic activity, endothelial mitogenic action, as well as immune modulating effects.

One method for modulating peripheral 5-HT levels is the chronic use of serotonin-selective reuptake inhibitor drugs (SSRIs) such as alaproclate, dapoxetine, etoperidone, citalopram, escitalopram, fluoxetine, fluvoxamine, paroxetine, sertraline and zimelidine. Of note however, all the above-mentioned are known to penetrate the BBB readily and thus have CNS activities in addition to their peripheral activities on modulating 5-HT levels. Indeed the SSRIs are routinely used for treating CNS conditions such as clinical depression, obsessive-compulsive disorder, and additional mood disorders and are hence known to belong to the class of antidepressant drugs.

Stemming from the vast research on serotonin it transpired that blocking the 5-HT transporter (5-HTT) activity in the periphery by SSRI drugs leads to decreased platelet 5-HT storage capacity, and thereby leads to reduced biological availability of platelet 5-HT. This in turn leads to reduced platelet aggregation during inflammation.

Several studies, including use of transgenic mice deficient in peripheral 5-HT synthesis, have suggested that reducing peripheral 5-HT levels may be beneficial for coronary artery disease (CAD) patients. In other words, reducing platelets 5-HT storage capacity is reflected in anti-thrombotic consequences. Indeed, epidemiological studies have indicated that patients who are treated chronically with SSRI drugs are less likely to suffer from MI and CAD [5-8].

Among the lines of evidence pointing towards potential beneficial effects of reduced peripheral 5-HT, is the observation that transgenic mice deficient in TPH1 (tph1−/−) and therefore in 5-HT synthesis exhibit reduced thrombosis risk [9].

There are several clinical studies showing that patients who take SSRI drugs chronically are less likely to develop thrombosis-related disorders, most notably, MI, stroke and CAD [7, 8, 10]. A randomized study compared sertraline (marketed under the name Zoloft as well as many other trade names) versus placebo in depressed post-acute coronary syndromes (ACS) patients, administered in addition to the standard antiplatelet agents aspirin and clopidogrel [10]. In this study, plasma markers of platelet activation were monitored, and the results showed that sertraline treatment was associated with substantially attenuated release of platelet/endothelial biomarkers as compared to the placebo treatment.

Furthermore, a multi-center study that included 68 hospitals, which focused on the effects of SSRI treatment on first time myocardial infarction (MI), indicated a protective effect: the odds ratio for MI among current SSRI users compared with nonusers was 0.35 [7].

The largest study to date compared 1080 myocardial infarction (MI) cases and 4256 controls during a 3-year period [8]. Unlike the former studies, this study included patients receiving various SSRIs (paroxetine, fluoxetine, or sertraline) as well as non-SSRI antidepressants and tricyclic antidepressants. The study reported that overall, SSRI use was associated with a large reduction of MI risk (odds ratio of 0.59; meaning, a 41% reduction of MI risk during the 3-year follow-up period); such reductions were not observed for the non-SSRI antidepressants. Notably, the two anti-platelet agents in current clinical use, aspirin and clopidogrel, were reported to reduce MI risk by only 20% and 10% respectively [1].

It should be noted that the prospective beneficial effects of SSRIs for reducing MI, CAD and ischemic risk are not necessarily limited to their direct capacity for reducing thrombosis. An additional and attractive mechanism of action for the observed clinical benefits in chronic heart failure (CHF) patients might reflect reduced endothelial mitogenesis following platelet-endothelial adhesion, and hence, reduced restenosis at the coronary arteries [11]. Coronary restenosis occurs as a result of exaggerated coronary endothelial mitogenesis, which might involve increased activation of endothelial cells by adhering platelets and serotonin released by the latter. It is further established that serotonin is mitogenic for endothelial cells.

Over the years, additional potential clinical indications for probable beneficial effects of SSRI or other serotonin-modulating compounds for non-psychiatric indications have been unveiled. These include chronic disorders for which increased platelet activity has been reported and implicated in the disease progression. This diseases and disorders include pulmonary hypertension, in which a 50% reduction in the risk of death was noted in SSRI users [12]; restenosis, following elective coronary stenting of native coronary arteries which was shown to be reduced by blocking the action of peripheral 5-HT [13]; rheumatoid arthritis [14], diabetes, where the SSRI drug fluvoxamine was shown to improve hepatic glucose uptake in a dog [15], autoimmune disorders (e.g., multiple sclerosis, psoriasis), where mice lacking the 5-HTT (a situation mimicking chronically blocking the 5-HTT with an SSRI drug) were shown to be less sensitive to induction of experimental autoimmune encephalomyelitis (EAE), a well-defined animal model of autoimmune disease of the central nervous system mimicking features of the human disease multiple sclerosis [16], kidney failure [17] and inflammatory bowel disease (IBD) [18].

In recent publications, a potential therapeutic application of 5-HTT inhibitors in human pulmonary arterial hypertension have also been suggested, where it was shown that transgenic mice over-expressing 5-HTT in smooth muscle develop pulmonary hypertension, indicating that blocking the 5-HTT with SSRI could be protective against this disorder [19].

However, currently, chronic treatment with SSRI drugs is reserved in the clinic for affective disorders (also known as mood disorders), most notably, depression and compulsive disorders, and is unwarranted as chronic treatment for people at risk of CAD, MI, stroke or other ischemic diseases, which forms a large segment of the population over the age of 50 years. This is mainly due to the severe adverse CNS-related side-effects of chronic SSRI treatment, such as nausea, drowsiness or somnolence, headache, clenching of teeth, extremely vivid and strange dreams, dizziness, changes in appetite, weight loss/gain, changes in sexual behavior (reduced libido), increased feelings of depression and anxiety which may sometimes provoke panic attacks, tremors, autonomic dysfunction including orthostatic hypotension, thoughts of suicide, depersonalization (derealization), flattened emotions and increased aggressiveness. Out of this list of known adverse effects, the three most frequently observed in SSRI users are decreased libido, flattened emotions and increased aggressiveness.

SUMMARY OF THE INVENTION

Serotonin is stored in blood platelets and is known to participate in many processes which occur in the peripheral system and therefore regulation of its levels and/or activity is a key step for therapy.

There is thus a widely recognized need for novel compounds, which would exhibit a serotonin reuptake inhibitory activity mainly in the periphery, and hence could be utilized in the treatment of various peripheral disorders, without entering the CNS and affecting brain 5-HT storage and actions in the brain.

Embodiments of the present invention relate to novel compounds for treating peripheral serotonin associated diseases and disorders, and, more particularly, to novel serotonin reuptake inhibitors and their use as therapeutic agents having a peripheral-restricted activity for treating peripheral serotonin associated diseases and disorders.

Thus, according to one aspect of the present invention there is provided a serotonin reuptake inhibitor (SRI) compound, being modified so as to include at least one positively charged group, which is selected such that the modified SRI compound retains its charge at physiological pH, while substantially retaining its serotonin reuptake inhibition activity.

According to further features in preferred embodiments of the invention described below, the positively charged group is a quaternary ammonium group.

According to further features in the described preferred embodiments the quaternary ammonium group has the formula:

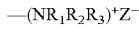

wherein:

Z is an organic or inorganic anion; and $R_1$, $R_2$ and $R_3$ are each independently selected from the group consisting of alkyl, aryl and cycloalkyl.

According to still further features in the described preferred embodiments, $R_1$, $R_2$ and $R_3$ are each independently an alkyl having from 1 to 4 carbon atoms.

According to still further features in the described preferred embodiments the alkyl is methyl.

According to still further features in the described preferred embodiments the positively charges group is a tertiary sulfonium group.

According to still further features in the described preferred embodiments the tertiary sulfonium group has the formula:

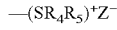

wherein:

Z is an organic or inorganic anion; and $R_4$ and $R_5$ are each independently selected from the group consisting of alkyl, aryl and cycloalkyl.

According to still further features in the described preferred embodiments, $R_4$ and $R_5$ are each independently an alkyl having from 1 to 4 carbon atoms.

According to still further features in the described preferred embodiments the alkyl is methyl.

According to still further features in the described preferred embodiments, the SRI compound presented herein is derived from a compound selected from the group consisting of a selective serotonin reuptake inhibitor (SSRI), a serotonin-norepinephrine reuptake inhibitor (SNRI) and a serotonin-noradrenaline-dopamine reuptake inhibitor (SNDRI).

According to still further features in the described preferred embodiments, the SSRI is selected from the group consisting of citalopram, alaproclate, dapoxetine, etoperidone, fluoxetine, fluvoxamine, paroxetine, sertraline, venlafaxine and zimelidine.

According to still further features in the described preferred embodiments, the SNRI is selected from the group consisting of desvenlafaxine, duloxetine, milnacipran, nefazodone and venlafaxine.

According to still further features in the described preferred embodiments, the SNDRI is selected from the group consisting of brasofensine, tesofensine and nomifensine.

According to still further features in the described preferred embodiments, the SRI compound presented herein is derived from citalopram.

According to still further features in the described preferred embodiments, the SRI compound presented herein is N-alkyl-citalopram.

According to still further features in the described preferred embodiments, the alkyl is methyl.

According to still further features in the described preferred embodiments, the SRI compound presented herein is substantially incapable of modulating a serotonin level and/or activity in the CNS.

According to still further features in the described preferred embodiments, the SRI compound presented herein is substantially incapable of reducing a serotonin level and/or activity in the CNS.

According to another aspect of the present invention there is provided N-alkyl-citalopram.

According to another aspect of the present invention there is provided N-methyl-citalopram.

According to another aspect of the present invention there is provided a process of preparing the SRI compound of claim 1, the process is effected by modifying the SRI compound so as to generate the at least one positively charged group.

According to further features in preferred embodiments of the invention described below, the SRI compound has an amine group.

According to still further features in the described preferred embodiments, modifying the SRI compound is effected by N-alkylating or N-arylating the amine group.

According to still further features in the described preferred embodiments, modifying the SRI is effected by alkylating agent selected from the group consisting of an alkyl-sulfonate, an aryl-sulfonate, an alkyleneimine, phosgene, an alkyl-tosylate, an aryl-tosylate, an alkyl-triflate, an aryl-triflate, an alkyl-halide, an aryl-halide, a dialkyl-sulfate, a diaryl-sulfate, an alumoxane, a trialkylaluminum and a tris(trialkylyl)aluminum.

According to still further features in the described preferred embodiments, the alkylating agent is methyl iodide.

According to another aspect of the present invention there is provided a method of modulating a level and/or activity of peripheral serotonin (5-HT) in a subject while substantially maintaining a level and/or activity of central serotonin in the subject, the method is effected by administering to the subject a SRI compound as presented herein.

According to another aspect of the present invention there is provided a use of an SRI compound as presented herein, in the modulation of a level and/or activity of peripheral serotonin (5-HT) in a subject while substantially maintaining a level and/or activity of central serotonin in the subject.

According to further features in the described preferred embodiments, the method of modulating a level and/or activity of peripheral serotonin (5-HT) in a subject is for treating a medical condition in which modulating a level and/or activity of peripheral serotonin (5-HT) in a subject while substantially maintaining a level and/or activity of central serotonin is beneficial.

According to still further features in the described preferred embodiments, the medical condition is selected from the group consisting of a cardiovascular disease or disorder, a cerebrovascular disease or disorder, ischemic heart disease (IHD), myocardial infarction (MI), cerebral stroke, pulmonary embolism, type-2 diabetes-associated vascular abnormalities, pulmonary arterial hypertension, peripheral arterial occlusive disease, rheumatoid arthritis, an autoimmune disorder, kidney failure, inflammatory bowel disease, acute coronary syndrome, coronary artery disease (CAD) and restenosis following coronary artery bypass post-grafting.

According to yet another aspect of the present invention there is provided a method of treating a disease or disorder in which reducing or preventing platelet aggregation and/or platelet-endothelial interactions is beneficial, the method is effected by administering to a subject in need thereof a therapeutically effective amount of an SRI compound as presented herein.

According to still another aspect of the present invention there is provided a use of an SRI compound as presented herein, in the treatment of a disease or disorder in which reducing or preventing platelet aggregation and/or platelet-endothelial interactions is beneficial.

According to yet another aspect of the present invention there is provided a use of an SRI compound as presented herein, in the manufacture of a medicament for the treatment of a disease or disorder in which reducing or preventing platelet aggregation and/or platelet-endothelial interactions is beneficial.

According to still another aspect of the present invention there is provided a pharmaceutical composition comprising, as an active ingredient, an SRI compound as presented herein and a pharmaceutically acceptable carrier.

According to further features in the described preferred embodiments, the pharmaceutical composition is packaged in a packaging material and identified in print, in or on the packaging material for use in the treatment of a medical condition in which modulating a level and/or activity of peripheral serotonin (5-HT) in a subject while substantially maintaining a level and/or activity of CNS serotonin is beneficial, as described herein.

According to further features in the described preferred embodiments, the pharmaceutical composition is packaged in a packaging material and identified in print, in or on the packaging material for use in the treatment of a disease or disorder in which reducing or preventing platelet aggregation and/or platelet-endothelial interactions is beneficial, as described herein.

According to further features in the described preferred embodiments, the SRI compound is substantially incapable of modulating a serotonin level in the CNS of the subject.

According to still further features in the described preferred embodiments, the SRI compound is substantially incapable of increasing a serotonin level or activity in the CNS of the subject.

According to still further features in the described preferred embodiments, the SRI compound is substantially incapable of reducing a serotonin level or activity in the CNS of the subject.

According to still further features in the described preferred embodiments, reducing or preventing platelet aggregation and/or platelet-endothelial interactions is effected while substantially maintaining a level and/or activity of CNS serotonin, thereby avoiding CNS-related effects.

According to still further features in the described preferred embodiments, the method of treatment, the pharmaceutical composition and the uses of the SRI presented herein further includes a therapeutically effective amount of an additional therapeutically active agent.

According to still further features in the described preferred embodiments, the additional therapeutically active agent is anti-platelet agent.

According to still further features in the described preferred embodiments, the anti-platelet agent is selected from the group consisting of aspirin, clopidogrel, abciximab, argatroban, cilostazol, danaparoid, dazoxiben, dipyridamole, eptifibatide, ticlopidine and tirofiban.

The present invention successfully addresses the shortcomings of the presently known configurations by providing novel serotonin reuptake inhibitors with peripheral-system-restricted activity, as well as compositions and methods utilizing same, which are far superior to the presently used SRIs by being substantially devoid of CNS effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "preventing" includes barring an organism from acquiring a condition in the first place.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
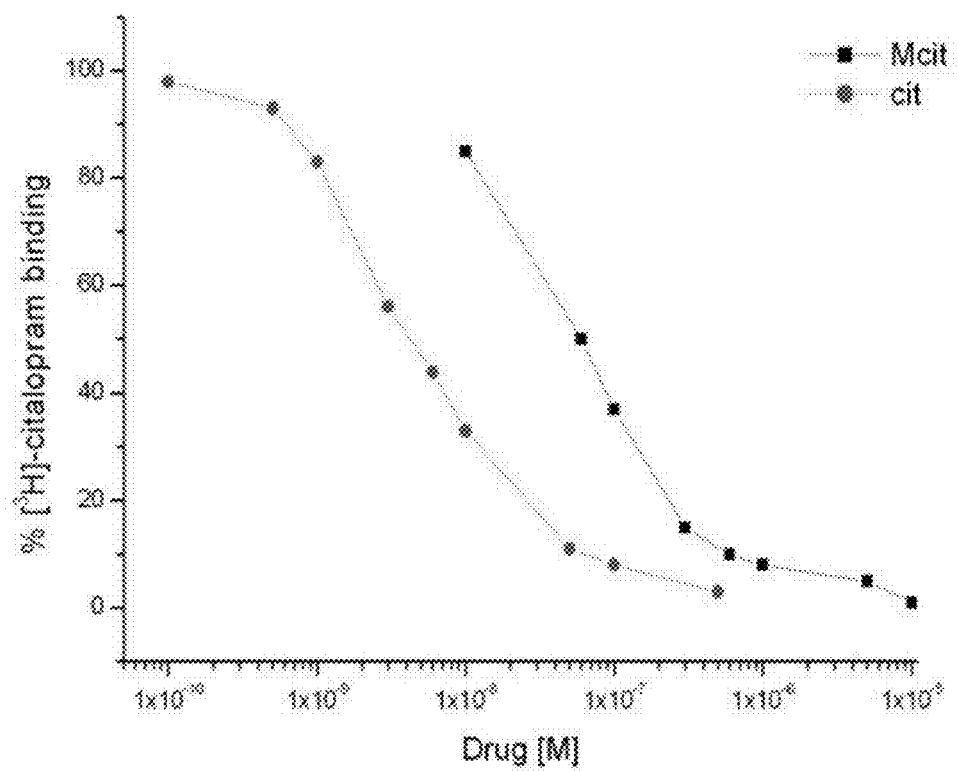
Figure 2:
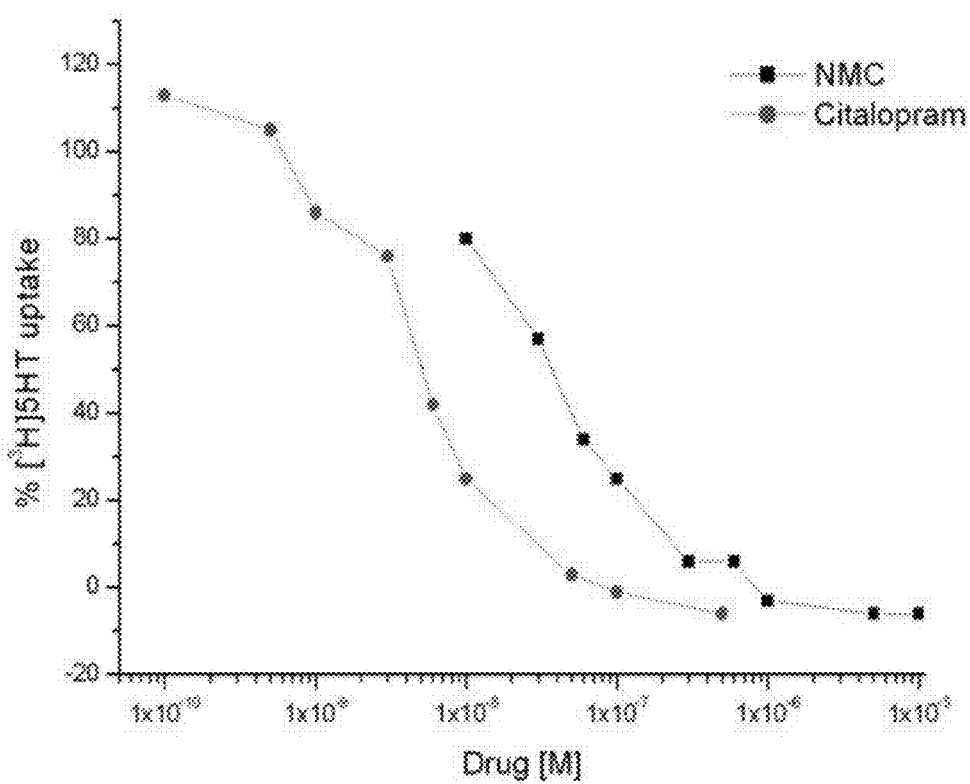
Figure 3:
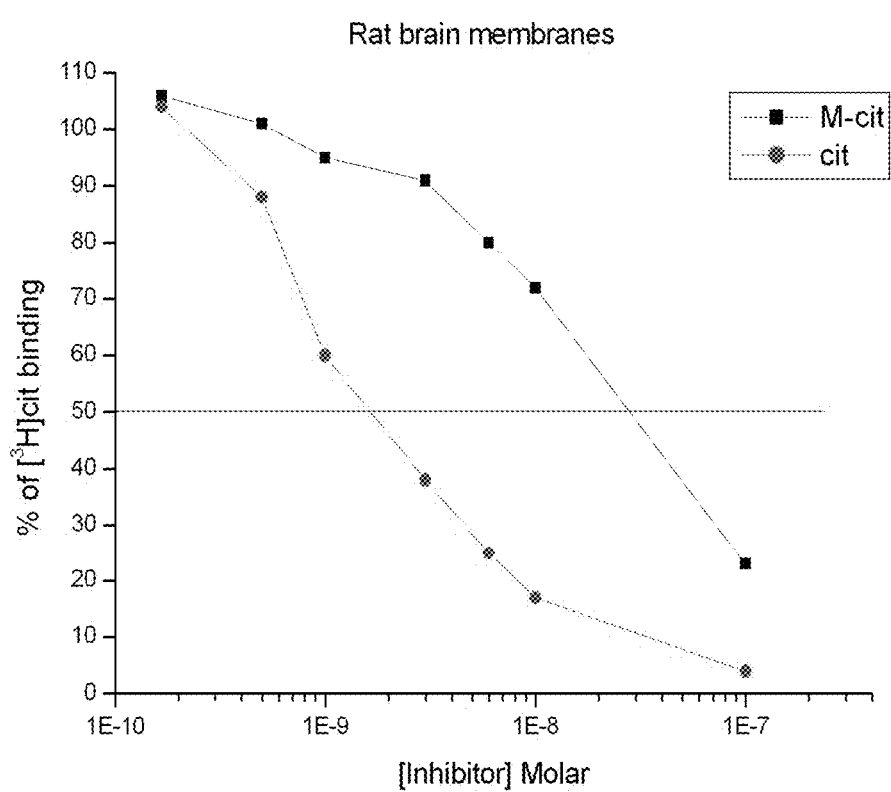
Figure 4:
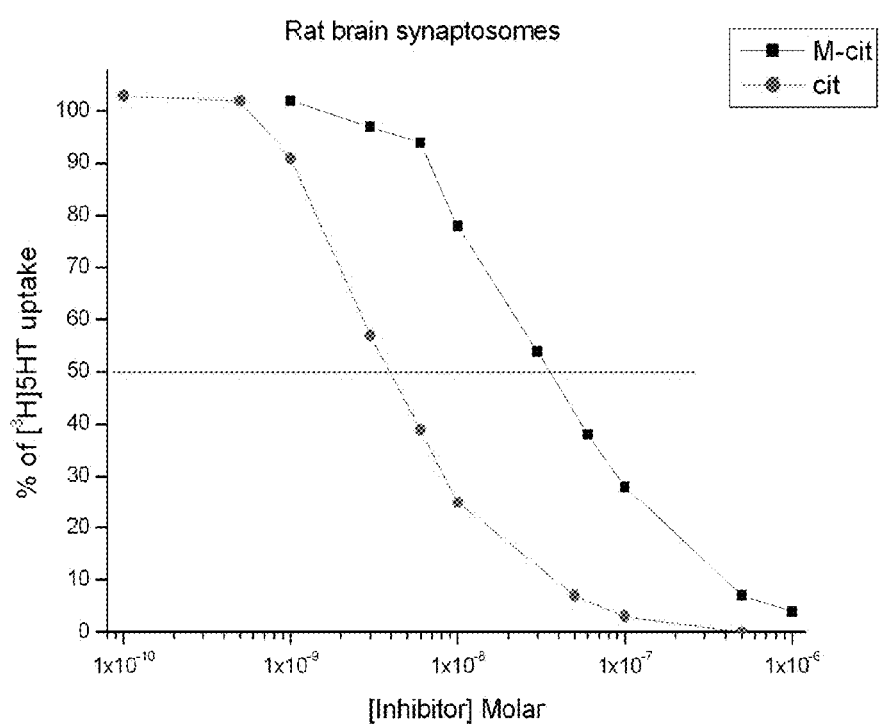
Figure 5:
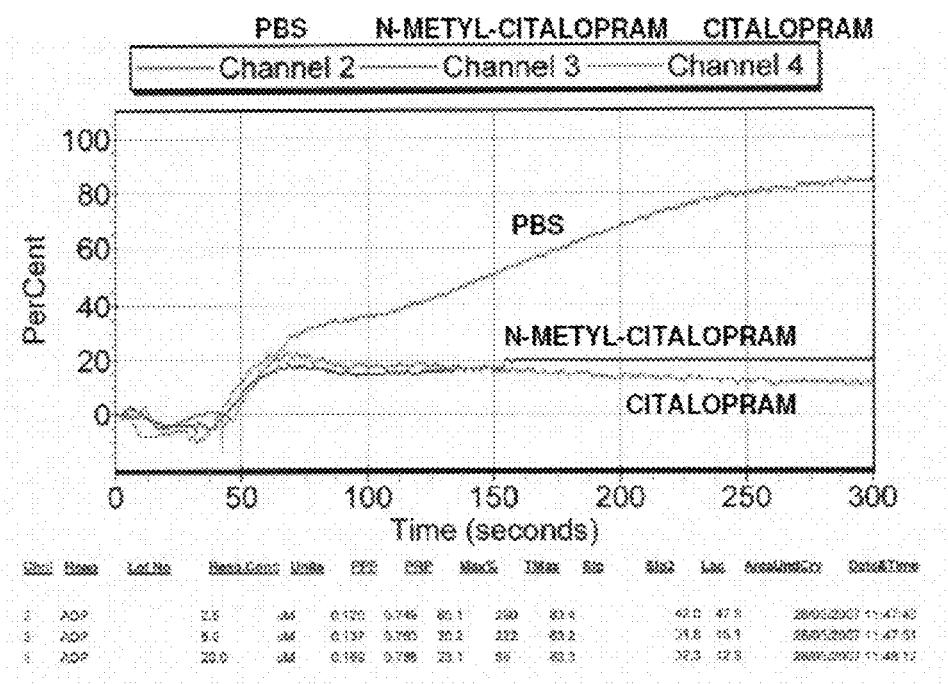
Figure 6:
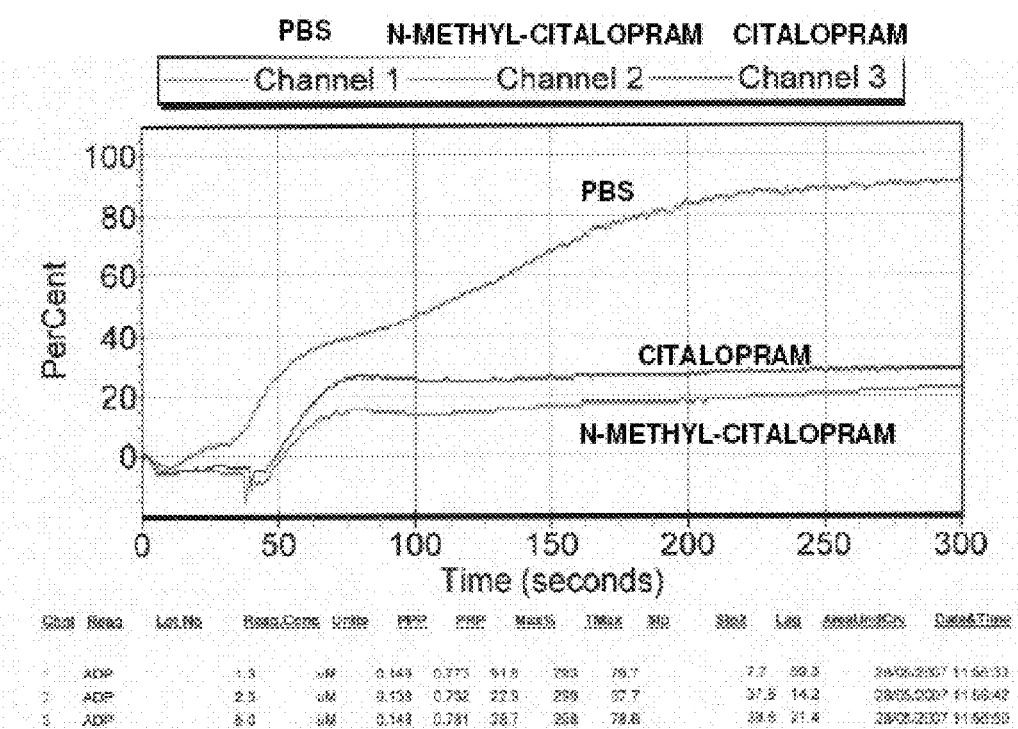
Figure 7:
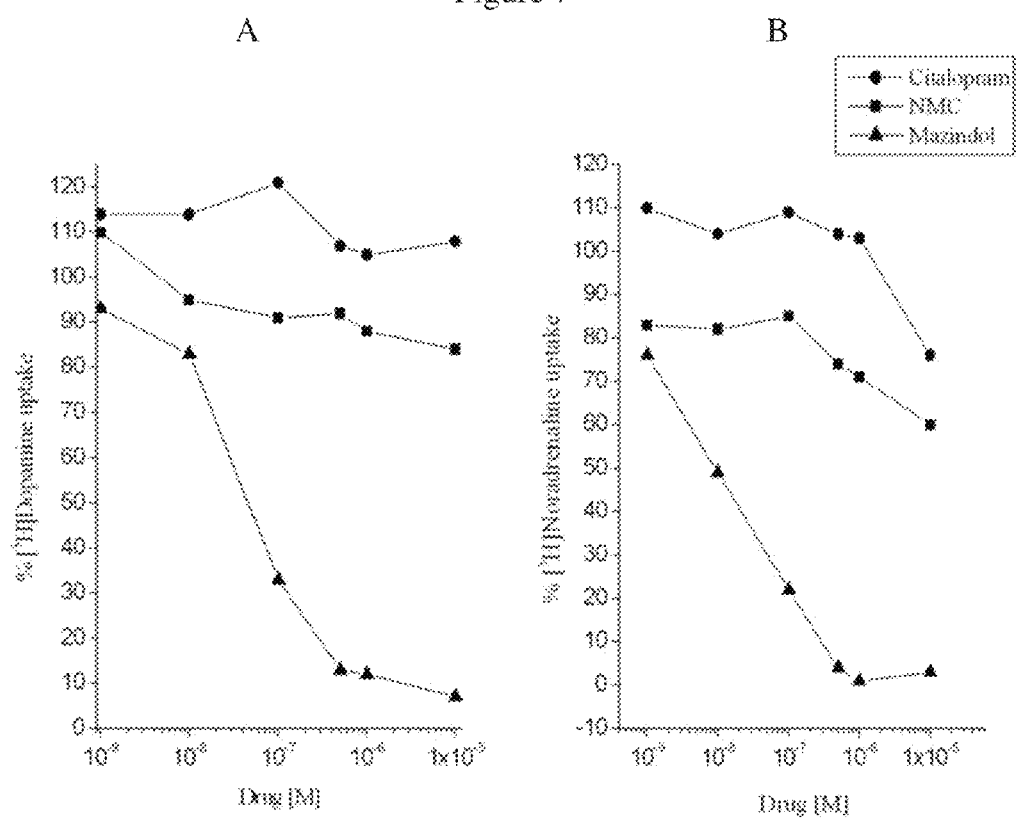

FIG. 1 presents comparative plots showing the inhibition of the binding of [$^3$H]citalopram (2 nM) to the human platelet membranes serotonin transporter (5-HTT) by N-methyl-citalopram (NMC, marked as "M-cit") or citalopram (marked as "cit") as a function of the concentration of the competitive inhibitor, and showing that NMC exhibits a lower binding affinity to 5-HTT as that of citalopram (Ki values of 62.00±8.3 nM for NMC and 6.32±1.10 nM for citalopram;

FIG. 2 presents comparative plots showing the inhibition of serotonin uptake in intact freshly prepared human platelets affected by the presence of the tested compounds, NMC (marked as "M-cit") and citalopram (marked as "cit"), expressed in percent of inhibition of the uptake of [$^3$H]serotonin uptake (50 nM) as a function of the concentration of the tested compounds, and showing an inhibition constant (Ki) value of 4.3±0.9 nM for citalopram and 52.0±15 nM for NMC;

FIG. 3 presents comparative plots showing the inhibition of the binding of [$^3$H]citalopram binding (1 nM) to rat brain membranes serotonin transporter (5-HTT) by N-methyl-citalopram (NMC; marked as "M-cit") or citalopram (marked as "cit") as a function of the concentration of the competitive inhibitor, and showing inhibition constant (Ki) values of 53±15 nM for NMC and 3±1 nM for citalopram;

FIG. 4 presents comparative plots showing the inhibition of serotonin uptake in freshly prepared rat brain synaptosomes effected by the presence of the tested compounds, NMC and citalopram, expressed in percent of inhibition of [$^3$H]serotonin uptake (50 nM), and showing inhibition constant (Ki) values of 44±6.6 nM for NMC and 4.5±0.7 nM for citalopram;

FIG. 5 presents comparative plots of the measurement of platelet aggregation as recorded for a sample from a healthy donor, showing the percent inhibition of human platelet aggregation effected by citalopram (plot denoted "Channel 4" and colored in brown), by N-methyl-citalopram (plot denoted "Channel 3" and colored in blue), and by the control PBS (plot denoted "Channel 2" and colored in red);

FIG. 6 presents a repeat of the experiment presented in FIG. 5 as measured for a sample taken from the same healthy donor, showing the percent inhibition of human platelet aggregation effected by citalopram (plot denoted "Channel 3" and colored in blue), by N-methyl-citalopram (plot denoted "Channel 2" and colored in red), and by the control PBS (plot denoted "Channel 1" and colored in green);

FIGS. 7A-B present plots of [$^3$H]dopamine uptake (FIG. 7A) and [$^3$H]noradrenaline uptake (FIG. 7B) into rat brain synaptosomes as a function of the concentration of a drug, comparing the inhibitory effect of citalopram, NMC and mazindol; and FIG. 8 presents comparative plots of the accumulation of [$^3$H]disintegration events per minute (DPM) in the cerebral cortex samples of mice after the indicated times following intraperitoneal injection of either [$^3$H]N-methyl-citalopram (marked in red circles) or [$^3$H]citalopram (marked in black rectangle) (values represent the mean+/−standard deviations for 3 mice for each compound and at each time point, with the exception of 40 minutes for which only a single mouse was injected with each compound).

DESCRIPTION OF THE PREFERRED EMBODIMENTS

The present invention is of novel compounds having serotonin reuptake inhibitory activity, which can be used as drugs in the treatment of diseases, disorders and medical conditions wherein regulation of serotonin levels in the peripheral system is beneficial. More specifically, the novel serotonin reuptake inhibitors presented herein exhibit their activity mainly in the peripheral system while not having a significant effect on the serotonin levels in the CNS, and can therefore be used beneficially to treat, for example, chronic diseases in which elevated platelets aggregation and increased platelet-endothelial interactions are part of the disease process, such as in the case of thrombosis and the related risks of ischemia, ischemic heart disease (IHD), myocardial infarction (MI), cerebral stroke, pulmonary embolism, and type-2 diabetes-associated vascular abnormalities, as well as other diseases and disorders in which inhibition of peripheral serotonin is beneficial.

As discussed hereinabove, when crossing the blood-brain barrier (BBB), serotonin reuptake inhibitors increase the extracellular level of serotonin by inhibiting reuptake thereof into the presynaptic cell and thereby increasing the level of serotonin available for binding to the postsynaptic receptor. In the peripheral system it has been shown that serotonin reuptake inhibitors reduce the levels of serotonin in the platelets which serve as storage vessels thereof and hence presently known serotonin reuptake inhibitors, particularly SSRIs were shown to have anti-platelet effects. Presently known SSRIs, which were developed as antidepressants, are required to penetrate the BBB and exert their effect on the CNS. However, SSRIs are known to cause several adverse CNS-related effects, such as nausea, drowsiness or somnolence, headache, clenching of teeth, extremely vivid and strange dreams, dizziness, changes in appetite, weight loss/gain, changes in sexual behavior (reduced libido), increased feelings of depression and anxiety, panic attacks, tremors, autonomic dysfunction including orthostatic hypotension, increased or reduced sweating, akathisia, depersonalization (derealization), flattened emotions and increased aggressiveness.

Therefore, albeit the amounting evidence that presently known SSRIs are potent drug candidates for many chronic medical conditions and even exhibit improved activity compared to other drugs, they are not prescribed for their treatment due to the severe CNS-related adverse effects.

While conceiving the present invention, the present inventors hypothesized that compounds having serotonin reuptake inhibitory (SRI) activity may be modified so as to reduce their capacity to cross the BBB. It was further hypothesized that presently known selective and non-selective serotonin reuptake inhibitors, jointly referred to herein as serotonin reuptake inhibitors (SRIs), modified chemically so as to have one or more charged groups while not affecting their SRI activity, could be used as drugs for treating medical conditions wherein modulating the peripheral serotonin level is beneficial. For example, modified SRIs which retain their ability to bind to the peripheral 5-HTT in platelets, would have potential anti-platelet activity similar to presently known SRIs. However, such modified SSRIs would not exhibit the highly undesired CNS-related adverse effects since charged molecules are known to lack the capacity to cross the BBB.

The underlying basis for this conception is based on the hypothesis that SRIs bind to 5-HTT based on molecular recognition factors which are not necessarily sensitive to changes in the overall charge of the compound. Furthermore, it has been assumed that charged compounds are unable to pass the blood-brain barrier (BBB) due to the unique structure of brain capillaries endothelial cells, which include tight junctions instead of gap junctions between capillary wall cells, thereby prohibiting the passage of charged molecules. Hence, modifying an SRI so as to have a charged group may have little or no effect on the binding affinity of the modified SRI to 5-HTT, but may have a major effect on its capacity to exert SRI activity in the brain.

While reducing the present invention to practice, the present inventors have demonstrated citalopram, one of the most widely prescribed SSRIs, as an exemplary test compound for such a modification, and prepared N-methyl-citalopram (NMC) which has a positively charged quaternary ammonium group, and a counter anion, marked as A$^-$ in the chemical structure illustration presented below. This quaternary ammonium group, by not being capable of participating in proton-exchange interactions, is positively charged at a wide range of pH levels, but most importantly, this group retains its positive charge at physiological pH.

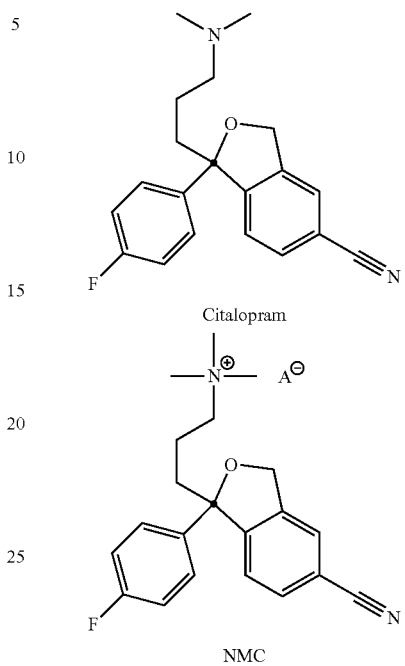

Citalopram

NMC

Citalopram (see chemical structure illustration above) is an SSRI antidepressant drug commonly used to treat depression associated with mood disorders, on occasions in the treatment of body dysmorphic disorder and anxiety. It's IUPAC name is 1-(3-Dimethylamino-propyl)-1-(4-fluoro-phenyl)-1,3-dihydro-isobenzofuran-5-carbonitrile, and it is marketed under the brand-names Celexa™ (U.S., Forest Laboratories, Inc.), Cipramil™, Citrol™, Sipralexa™, Seropram™ (Europe and Australia), Zetalo (India), Celepram™, Clazil™ (Australia), Zentius™ (South America, Roemmers) and Cipram™ (Denmark, H. Lundbeck A/S).

Citalopram is typically sold as a racemic mixture, consisting of 50% of the R-(−)-citalopram enantiomer and 50% of the S-(+)-citalopram enantiomer. However, it has been found that only the S-(+) enantiomer has the desired antidepressant effect, and therefore Lundbeck markets the S-(+) enantiomer, under the generic name of escitalopram. While citalopram is supplied as a hydrobromide salt, escitalopram is sold as the oxalate salt, and in both products the salt form allows these otherwise lipophilic compounds to dissolve in water.

As demonstrated in the Examples section that follows, NMC has been synthesized and shown to: (a) bind and inhibit the activity of the platelet serotonin transporter (5-HTT) with similar affinity as its parent compound citalopram; (b) bind and inhibit the activity of the brain serotonin transporter with about 10-fold lower affinity compared with its parent compound citalopram; and (c) have a substantially limited capacity to penetrate the BBB.

Hence, according to one aspect of the present invention, there is provided a serotonin reuptake inhibitor (SRI) compound, being modified so as to include at least one positively charged group which is selected such that the modified SRI compound retains its charge at physiological pH, while substantially retaining its SRI activity. Herein and throughout the SRI compounds presented herein which are being modified so as to include at least one positively charged group, are referred to interchangeably as modified SRIs or modified SRI compounds.

The phrase "serotonin reuptake inhibitor compound", abbreviated herein to SRI, as used herein, refers to compounds having the capacity to modulate the levels of serotonin in the body by inhibiting its re-absorption by the molecular transporter, 5-HTT. More specifically, SRIs exhibit competitive inhibition of 5-HTT. Serotonin reuptake inhibitors can be sorted into families according to their specificity, hence selective serotonin reuptake inhibitor (SSRI), include alaproclate, citalopram, escitalopram, etoperidone, fluoxetine, fluvoxamine, paroxetine, sertraline and zimelidine, serotonin-norepinephrine reuptake inhibitor (SNRI), include desvenlafaxine, duloxetine, milnacipran, nefazodone and venlafaxine, and serotonin-noradrenaline-dopamine reuptake inhibitor (SNDRI), include brasofensine, tesofensine and nomifensine.

According to preferred embodiments, the serotonin reuptake inhibitor (SRI) compound is a serotonin-selective reuptake inhibitor (SSRI).

The phrase "positively charged group", as used herein, refers to an atom or a group of atoms which forms a part of an organic molecule, and which is characterized by a positive electrostatic charge. Compounds which include one or more positively charged groups are molecular ions oftentimes referred to as molecular cations. A positively charged group of atoms has at least one electron less than the number of protons in these atoms. Positively charged groups include, for a non-limiting example, ammonium and sulfonium groups.

A positively charged group which retains its charge at physiological pH is a group that is not capable of participating in proton-exchange interactions at a pH range which is typical to the physiological environment in the body where the SRI is active. Typically, the physiological pH is about 7.4; therefore a positively charged group which retains its charge at physiological pH refers to a positively charged chemical group that stays ionized in a pH range of about 5-8. It is noted that even in the GI, where the pH level is extremely low in terms of physiological pH, the positively charged group according to preferred embodiments remains positively charged, and hence modified SRI compounds according to the present invention designed for oral administration, are not adversely affected by the GI pH levels.

Quaternary ammonium groups are known to be positively charged at any pH range, including the physiological pH range, hence the positively charged group, according to preferred embodiments of the present invention, is a quaternary ammonium group.

The phrase "quaternary ammonium", as used herein, refers to a nitrogen atom which forms a part of a molecule (an amine, as defined hereinbelow) that is attached to four non-hydrogen substituents and thus is positively charged.

Hence, according to preferred embodiments, the SRI is modified so as to have a quaternary ammonium group which has the general formula:

—(NR$_1$R$_2$R$_3$)$^+$Z$^-$ wherein:

Z is an organic or inorganic anion; and

R$_1$, R$_2$ and R$_3$ are each independently selected from the group consisting of alkyl, aryl and cycloalkyl.

Preferably, R$_1$, R$_2$ and R$_3$ are each an alkyl having from 1 to 4 carbon atoms, and more preferably, R$_1$, R$_2$ and R$_3$ are each methyl, resulting in the positively charged group, or the quaternary ammonium group —(NMe$_3$)$^+$.

As used herein, the term "amine" describes a —NR'R" group where each of R' and R" is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. Preferably, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halide, a hydroxy, an alkoxy and a hydroxyalkyl as these terms are defined hereinbelow. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

The positively charged group can be formed on the SRI from an existing group which forms a part of the SRI, namely, by turning a partially charged or uncharged group into a positively charged group, or by turning an existing positively charged group which can participate in proton-exchange interaction into one that cannot participate in such interaction, making it into an irreversible positive charge, or a permanent positive charge, thereby modifying the SRI.

Alternatively, the positively charged group can be added to the SRI by substituting one or more carbon atom with a positively charged group, e.g., by replacing a hydrogen atom or any other substituent with a quaternary ammonium or a tertiary sulfonium group.

The present embodiments further encompass any enantiomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable" and "pharmaceutically acceptable" are interchangeably used and refer to an approved substance that does not cause significant irritation to an organism and does not abrogate the biological activity and properties of the administered agent.

Since the modified SRI according to the present embodiments is a charged compound by definition, namely it is in a cation form, the phrase "pharmaceutically acceptable salt" refers to other charged species of the SRI compound, i.e. zwitterion or multiple charged species thereof and its counter ion(s), which is typically used to modify the solubility characteristics of the parent compound and/or to reduce any significant irritation to an organism by the parent compound, while not abrogating the biological activity and properties of the administered compound. Non-limiting examples for an anion include chloride, bromide, oxalate, maleate, mesylate and the like.

According to further preferred embodiments, the SRI is modified so as to have a sulfonium group which has the general formula:

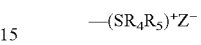

wherein:

Z is an organic or inorganic anion; and $R_4$ and $R_5$ are each independently selected from the group consisting of alkyl, aryl and cycloalkyl.

$R_4$, and $R_5$ are preferably each an alkyl having from 1 to 4 carbon atoms, and more preferably, $R_4$ and $R_5$ are each methyl, resulting in the positively charged group, or the sulfonium —$(SMe_2)^+$.

The term "sulfonium", as used herein, refers to a —$S^+R'R''$, wherein R' and R'' are each independently alkyl, cycloalkyl, heteroalicyclic, aryl or heteroaryl.

Exemplary SRIs from which the compounds described herein can be derived include, without limitation, SSRIs such as citalopram, alaproclate, dapoxetine, etoperidone, fluoxetine, fluvoxamine, paroxetine, sertraline, venlafaxine and zimelidine. These compounds are presented in Table 1 below.

Other SRIs which inhibit the reuptake of serotonin, including, for example, SNRIs and SNDRIs such as, for example, desvenlafaxine, duloxetine, milnacipran, nefazodone, venlafaxine, brasofensine, tesofensine and nomifensine, may also be modified so as to have a positively charged group, and be used in a similar way as the SSRIs presented herein.

Table 1 presents some of the presently known SSRI including their trade names and chemical structure.

TABLE 1

| SSRI Name | Trade name(s) | Structure |
|---|---|---|
| Alaproclate | N/A | 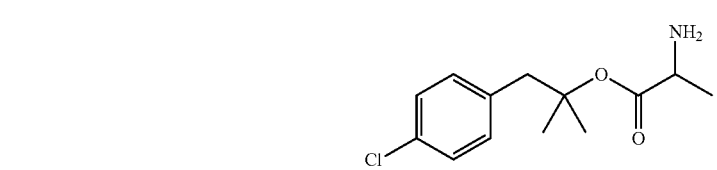 [SMILES: CC(N)C(=O)OC(C)(C)Cc1ccc(Cl)cc1] |
| Etoperidone | N/A | 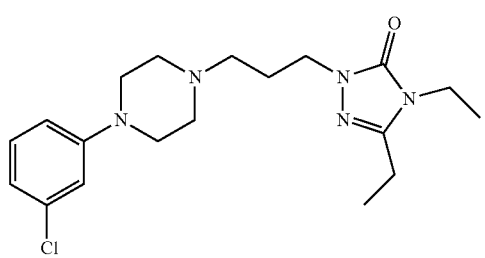 [SMILES: CCc1nn(CCCN2CCN(c3cccc(Cl)c3)CC2)c(=O)n1CC] |

TABLE 1-continued

| SSRI Name | Trade name(s) | Structure |
|---|---|---|
| Citalopram | Celexa, Cipramil, Seropram, Celepram, Ciazil, Emocal, Sepram, Seropram | 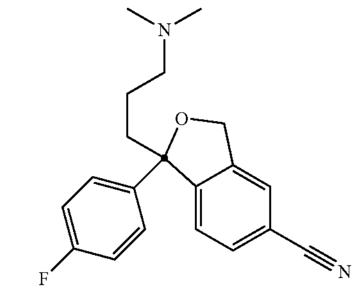 |
| Escitalopram | Lexapro, Cipralex, Esteria | 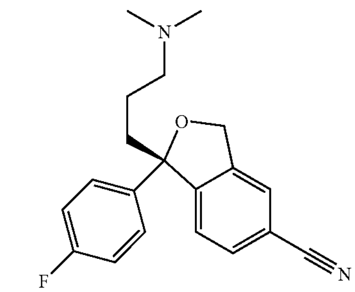 [SMILES: CN(C)CCC[C@@]1(c2ccc(F)cc2)OCc2cc(C#N)ccc21] |
| Fluoxetine | Prozac, Fontex, Seromex, Seronil, Sarafem, Fluctin | 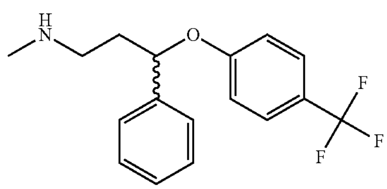 [SMILES: CNCCC(Oc1ccc(C(F)(F)F)cc1)c1ccccc1] |
| Fluvoxamine | Luvox, Faverin, Fevarin Dumyrox | 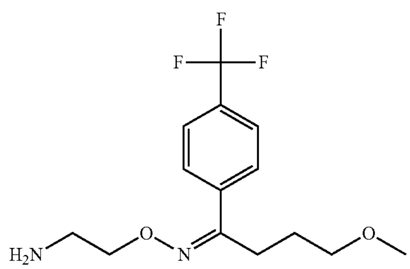 [SMILES: COCCC/C(=N/OCCN)c1ccc(C(F)(F)F)cc1] |
| Paroxetine | Paxil, Seroxal, Aropax, Deroxat, Rexetin, Xetanor, Paroxat | 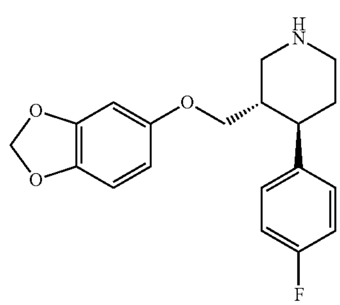 [SMILES: Fc1ccc([C@@H]2CCNC[C@H]2COc2ccc3c(c2)OCO3)cc1] |
| Sertraline | Zoloft, Sertralin, Lustral, Apo-Sertral, Asentra, Gladem, Serlift, Stimuloton, Xydep, Serlain, Concorz | 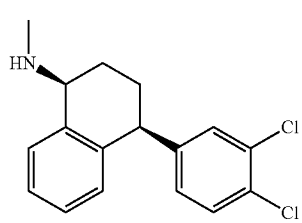 [SMILES: CN[C@H]1CC[C@@H](c2ccc(Cl)c(Cl)c2)c2ccccc21] |

TABLE 1-continued

| SSRI Name | Trade name(s) | Structure |
|---|---|---|
| Dapoxetine | N/A | 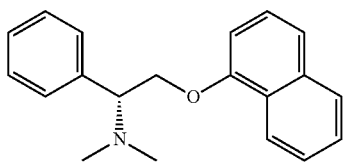 [SMILES: CN(C)[C@@H](COc1cccc2ccccc12)c1ccccc1] |
| Venlafaxine | Depurol, Dobupal, Efectin, Efexor, Elafax, Faxine, Flavix, Norpilen, Trevilor, Vandral, Velafax, Venlafaxina, Venlax, Venlor, Viepax | 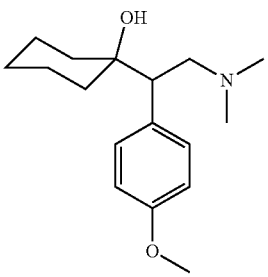 [SMILES: COc1ccc(C(CN(C)C)C2(O)CCCCC2)cc1] |
| Zimelidine | Normud, Zelmid | 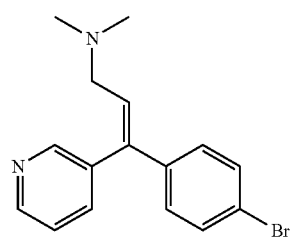 [SMILES: CN(C)C/C=C(/c1ccc(Br)cc1)c1cccnc1] |

As can be seen in Table 1, all these SSRIs comprise at least one amine group, which can be readily converted into a quaternary ammonium, i.e. a positively charged group. As can further be seen in Table 1, all these SSRIs offer a multitude of substitution positions on which a positively charged group can be added. One of the requirements for these chemical modifications is the retention of the SSRI activity.

For example, etoperidone can be methylated at one or both of the piperazine nitrogen atoms which will turn each of these amines into a quaternary ammonium. Fluvoxamine can be modified so as to have one of the aliphatic carbon atoms substituted with a thiol group, which can be further modified into a tertiary sulfonium group.

As mentioned hereinabove, the present inventors selected citalopram as a model to demonstrate the present embodiments, and prepared N-methyl-citalopram (NMC), as exemplified in the Examples section that follows. As further demonstrated in the Examples section that follow, NMC was found to be a promising drug candidate for a peripherally-acting SSRI drug lacking CNS activity.

As is demonstrated in the Examples section that follows, NMC recognized the human platelet 5-HTT with lower affinity as compared to citalopram, shown by competition binding experiments in human platelet membranes, using [$^3$H]citalopram as a detectible marker. NMC was also shown to inhibit [$^3$H]5-HT uptake by freshly isolated human platelets, yet in a higher inhibition constant (Ki) value than determined for citalopram.

NMC was about one-order of magnitude less potent than citalopram in binding to and inhibiting 5-HTT in rat brain.

NMC appears to penetrate the BBB to a much lower extent than citalopram, at levels that were near the detection threshold in the performed experiments. It is estimated that the brain penetration of N-methyl-citalopram following its intraperitoneal injection is about 50-fold less than that of citalopram.

Citalopram and NMC both exhibited strong inhibition of human platelet aggregation.

These data therefore demonstrate that NMC is a potent anti-platelet drug, whereby being a quaternary nitrogen (quaternary ammonium)-containing compound (positively charged at any physiological pH) renders its capability to cross the BBB substantially limited. Therefore, NMC and other modified (e.g., quaternary ammonium-containing) SRI compounds are potent anti-platelet agents (decreasing platelet aggregation) which are devoid of the undesired CNS effects of presently known SRIs.

According to another aspect of the present invention, there is provided a process of preparing the SRI presented herein, the process is effected by modifying an SRI so as to include one or more positively charged group which retains its charge at physiological pH, while substantially retaining its SRI activity.

Preferably, the process is effected by alkylating or arylating an existing chemical group on the SRI, such as an amine group. Alternatively, an amine group and/or a sulfonium group can be added to the SRI.

When alkylating or arylating a pre-existing amine group, the process is effected by N-alkylating or N-arylating this amine group.

N-Alkylation and N-arylation are typically effected by utilizing an alkylating/arylating agent. The phrase "alkylating/ arylating agent", as used herein, refers to a chemical reagent which use thereof can place an alkyl or an aryl, as this is define herein, at a designated position on a given reactant compound.

Exemplary alkylating or arylating agents include, without limitation, an alkyl- or arylsulfonate, an alkyleneimine, phosgene, an alkyl- or aryl-tosylates, an alkyl- or aryl-triflates, an alkyl- or aryl-halide, a dialkyl- or diaryl-sulfate, an alumoxanes, a trialkylaluminum and a tris(trialkylyl)aluminum. Preferably the alkylating agent is methyl iodide.

Alkylation (methylation) reactions are commonly used and practiced on amines and other chemical groups for many decades, and may involve other preparative steps such as conversion of a charged amine in a water soluble parent compound into the organic-solvent soluble free-base form thereof, typically by means of a bi-phasic reaction with a mild base, such as sodium bicarbonate, which allows the free-base form of the parent compound to cross to the organic phase once losing its charge.

The phrase "free-base form", as used herein, refers to a standalone basic form of a non-quaternary amine group, as opposed to its water-soluble ammonium salt form. For example R—$NH_2$ is the free-base form of R—$NH_3^+$.

Following similar synthetic paths, additional novel SRIs having a positively charged group can be obtained by a single, double or triple N-methylation of an amine group which already form a part of the molecule, including, for example, N,N,N-trimethyl-alaproclate, N-methyl-dapoxetine, N-methylpiperazin-etoperidone, N,N-dimethyl-fluoxetine, N,N, N-trimethyl-fluvoxamine, N,N-dimethylpiperidine-paroxetine, N,N-dimethyl-sertraline and N-methyl-venlafaxine.

As discussed hereinabove and demonstrated in the Examples section that follows, an SRI modified to have at least one positively charged group is a very promising drug candidate that can be beneficially used to treat medical conditions which are associated with peripheral serotonin levels.

According to another aspect of the present invention, there is provided a method of modulating a level and/or activity of peripheral serotonin (5-HT) in a subject while substantially maintaining a level and/or activity of central serotonin in the subject, the method is effected by administering to the subject an SRI modified so as to comprise at least one positively charged group which retains its charge at physiological pH, while substantially retaining its SRI activity.

Accordingly, there is provided a use of the modified SRI as presented herein in the modulation of a level and/or activity of peripheral serotonin (5-HT) in a subject while substantially maintaining a level and/or activity of central serotonin in the subject.

The phrase "modulating the level and/or activity" as used herein refers to the result of an intended action which indirectly alters (increase or decrease) the concentration (level), and/or the activity of a substance at certain intended bodily sites in a subject.

The phrase "substantially maintaining a level and/or activity" as used herein, means the opposite of the previous definition, namely, the concentration (level), and/or the activity of a substance at certain intended bodily sites in a subject does not alter (increase or decrease) as a result of an intended action.

In the context of the present embodiments, the modified SRI presented herein have the ability to modulate the level and/or activity of serotonin in the peripheral system while at the same time not affecting (substantially maintaining) the level and/or activity of serotonin in the CNS.

According to preferred embodiments, this method of modulating a level and/or activity of peripheral serotonin can be used for treating certain medical conditions in which this type of modulating is beneficial. Such medical conditions include, without limitation, cardiovascular diseases or disorders, cerebrovascular diseases or disorders, ischemic heart disease (IHD), myocardial infarction (MI), cerebral stroke, pulmonary embolism, type-2 diabetes-associated vascular abnormalities, pulmonary arterial hypertension, peripheral arterial occlusive disease, rheumatoid arthritis, autoimmune disorders, kidney failure, inflammatory bowel disease, acute coronary syndrome, coronary artery disease (CAD) and restenosis following coronary artery bypass post-grafting.

As discussed hereinabove, peripheral serotonin levels have been implicated mainly with platelet aggregation, and in turn, platelet aggregation has been implemented with several medical conditions, most of which are highly lethal. These include cardiovascular diseases or disorders, IHD, MI, stroke, pulmonary embolism, diabetes-associated vascular abnormalities, pulmonary hypertension and arterial occlusive diseases, as well as preventive measures against clot formation and other prophylactic anti-embolic treatments.

Hence, according to yet another aspect of the present invention, there is provided a method of treating a disease or disorder in which reducing or preventing platelet aggregation and/or platelet-endothelial interactions is beneficial, the method is effected by administering to a subject in need thereof a therapeutically effective amount of the SRI modified so as to comprise at least one positively charged group which retains its charge at physiological pH, while substantially retaining its SRI activity.

The term "therapeutically effective amount" or "pharmaceutically effective amount" denotes that dose of an active ingredient or a composition comprising the active ingredient that will provide the therapeutic effect for which the active ingredient is indicated.

Accordingly, there is provided a use of the modified SRI as presented herein in the treatment of a disease or disorder in which reducing or preventing platelet aggregation and/or platelet-endothelial interactions is beneficial.

In all the methods and uses presented herein, the modified SRI is substantially incapable of modulating the serotonin level in the CNS of a subject, may it be increasing or decreasing CNS serotonin levels, thereby avoiding CNS-related effects.

The SRIs of the present invention when used, for example, as preventive measures against clot formation or a prophylactic anti-embolic treatment, can be utilized in combination with an additional therapeutic agent, preferably an anti-platelet agent and other inhibitors of platelet function.

Examples of useful inhibitors of platelet function include, but are not limited to acadesine, anagrelide (given at doses exceeding 10 mg/day), anipamil, argatroban, aspirin, clopidogrel, cyclooxygenase inhibitors such as nonsteroidal anti-inflammatory drugs and the synthetic compound FR-122047, clofibrate, caffeine, danaparoid sodium, dazoxiben hydrochloride, diadenosine 5',5''-P1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin ($PGI_2$), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and any other anti-serotonin drug.

More preferably, the anti-platelet agent is aspirin, clopidogrel, abciximab, argatroban, cilostazol, danaparoid, dazoxiben, dipyridamole, eptifibatide, ticlopidine or tirofiban.

Other therapeutic agents which may be used beneficially to treat medical conditions which are associated with platelet aggregation include anticoagulants such as heparin, warfarin, acenocoumarol, phenprocoumon, phenindione and hirudin, as well as nitric oxide (NO) donating agents.

The modified SRIs presented herein can be utilized per-se or as a part of a pharmaceutical composition, hence, according to still another aspect of the present invention, there is provided a pharmaceutical composition which include, as an active ingredient, the SRI presented herein and a pharmaceutically acceptable carrier.

The pharmaceutical compositions or medicaments presented herein may include additional therapeutic agents, as these are discussed hereinabove.

As used herein a "pharmaceutical composition" refers to a preparation of the SRI presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered SRI. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the SRIs into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising an SRI of the invention formulated in a compatible pharmaceutical carrier may also be prepared, placed in an appropriate container, and labeled for treatment of a particular medical condition, disease or disorder, as is detailed hereinabove.

According to preferred embodiments, the pharmaceutical composition is being packaged in a packaging material and identified in print, in or on the packaging material for use in the treatment of a medical condition in which modulating a level and/or activity of peripheral serotonin (5-HT) in a subject, while substantially maintaining a level and/or activity of central serotonin, is beneficial, as these are discussed hereinabove.

According to other preferred embodiments, the pharmaceutical composition is being packaged in a packaging material and identified in print, in or on the packaging material for use in the treatment of a disease or disorder in which reducing or preventing platelet aggregation and/or platelet-endothelial interactions is beneficial, as these are discussed hereinabove.

Accordingly, there is provided a use of the modified SRI as presented herein in the manufacture of a medicament for treating a disease or disorder in which reducing or preventing platelet aggregation and/or platelet-endothelial interactions is beneficial.

Alternatively, there is provided a use of the modified SRI as presented herein in the manufacture of a medicament for treating a medical condition in which modulating a level and/or activity of peripheral serotonin (5-HT) in a subject while substantially maintaining a level and/or activity of central serotonin is beneficial.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Citalopram, serotonin (5-HT), fluoxetine, mazindol, dopamine and noradrenaline of the highest obtainable purity were obtained from Sigma-Aldrich Israel Ltd.

[$^3$H]Serotonin ([$^3$H]5-HT, 20.3 Ci/mmol), [$^3$H]Citalopram (79 Ci/mmol), [$^3$H]Dopamine (55.1 Ci/mmol) and [$^3$H]Ketanserin (76 Ci/mmol), were obtained from Perkin Elmer Life Sciences (Boston, Mass., USA).

[$^3$H]Noradrenaline (35 Ci/mmol) was purchased from Amersham, GE Healthcare UK.

Homogenization of samples was conducted using a Kinematica Polytron® Homogenizer device, Westbury, N.Y., USA.

Brain tissue samples were grinded using a Potter-Elvehjem, PTFE pestle and glass tube grinder.

Tritium concentration, expressed in DPM, was determined using a β-emission liquid scintillation analyzer, Tri-Carb 2100TR by Packard.

Male Wistar rats and Imprinting Control Region (ICR) mice (Harlan laboratories, Israel) were maintained under controlled light and temperature conditions, with food and water provided ad libitum.

Animal procedures were approved by the Animal Care Committees of Tel-Aviv University (Approval numbers: M-06-105, M-07-027).

The independent samples t-test, using SPSS software (SPSS Inc. Chicago, Ill.), was used as appropriate. Results are expressed as means±S.E.M.

Preparation of N-methyl-citalopram:

N-methyl-citalopram (NMC, 1.8 grams) was synthesized from of the free-base form of the parent compound citalopram via methylation by methyl iodide. Saturated solution of sodium bicarbonate (20 ml) was added to a solution of citalopram (1 gram) in dichloromethane (20 ml). The reaction mixture was mixed for a few minutes, and then was allowed to separate to two phases. The organic phase was concentrated under reduced pressure to give 0.5 grams of the free-base form of citalopram that was used in the next step without further purification.

Methyl Iodide (10 equivalents) was added to a cool solution the free-base form of citalopram (1 gram, 3.08 mmol) in acetone. The mixture was heated to reflux over night, and thereafter the solvent was removed under reduced pressure to produce N-methyl citalopram (NMC, 0.5 grams, 1.5 mmol, 50 5 yield). The purity of NMC and the absence of citalopram were verified by HPLC.

Preparation of [$^3$H]N-methyl-citalopram:

[$^3$H]Methyl iodide (C[$^3$H]$_3$I), at specific activity of 70 Ci/mmol, was vacuum transferred into a tritiation production vessel containing the free base form of citalopram. Following several hours of incubation all volatiles were removed via distillation under reduced pressure. The crude residue was purified by HPLC to yield [$^3$H]N-methyl-citalopram, at more than 99% radiochemical purity.

Preparation of Human Platelet Membrane for Binding Assays:

Human blood samples (25 ml) were collected in the morning (between 8 and 10 AM) from healthy volunteers into plastic tubes containing 1 mM EDTA as anticoagulant. Platelet-rich plasma was separated from blood cells by low-speed centrifugation (350 g for 10 minutes), diluted in 20 ml of 50 mM Tris/HCl buffer pH 7.4 (containing 120 mM NaCl and 5 mM KCl) and centrifuged at 1700 g for 20 minutes. The supernatant was discarded and the final membrane pellet was kept frozen at −70° C. until used, usually within 2 days.

On the day of use, the platelet membrane pellet was disrupted with Brinkman polytron in 20 ml of 50 mM Tris HCl buffer pH 7.4 (containing 120 mM NaCl and 5 mM KCl) and centrifuged twice at 27,000 g for 20 minutes. It was then resuspended in 9 ml buffer to yield a final protein concentration of about 0.8 mg/ml.

Assay of [$^3$H]Citalopram Binding to Human Platelets:

[$^3$H]Citalopram binding to 5-HT transported (5-HTT) was determined using a method modified from Plenge et al. [20]. A standard binding assay contained: 200 of homogenate, 100 μl [$^3$H]citalopram (2 nM) and 50 μl buffer or test drug. After a 60 minutes incubation period at 25° C., homogenates were diluted in 3 ml ice-cold buffer and filtered through Whatman GF/C glass fiber filters. Filters were washed three times with 3 ml ice-cold buffer, and the radioactivity was measured in scintillation liquid in a β-counter. Specific binding was defined as the difference between total [$^3$H]citalopram binding (triplicate samples) and the binding in the presence of 10 μM fluoxetine (duplicate samples).

Assay of [$^3$H]Citalopram Binding to Rat Brain Membranes:

Rat brain cortex was disrupted with Brinkman polytron in 50 volumes of 50 mM Tris HCl buffer, pH 7.4 (containing 120 mM NaCl and 5 mM KCl) and centrifuged (three times) at 30,000 g for 10 minutes. It was then resuspended in the same buffer to yield a final concentration of about 21 mg/ml (wet weight). [$^3$H]Citalopram binding was determined using a method modified from Plenge et al. [20]. A standard binding assay contained: 100 μl of homogenate, 100 [$^3$H]citalopram (1 nM) and 300 μl buffer or 250 μl buffer and 50 μl test drug. After a 60-minutes incubation period at 25° C., homogenates were diluted in 3 ml ice-cold buffer and filtered through Whatman GF/C glass fiber filters. Filters were washed three times with 3 ml ice-cold buffer, and the radioactivity was measured in scintillation liquid in a β-counter. Specific binding was defined as the difference between total [$^3$H]citalopram binding (triplicate samples) and the binding in the presence of 10 μM fluvoxamine (duplicate samples).

Isolation of Human Platelets for Measuring [$^3$H]5-HT Uptake:

Human blood samples (25 ml) were collected in the morning (between 8 and 10 AM) from healthy volunteers into plastic tubes containing 1 mM EDTA as anticoagulant. Platelet-rich plasma (PRP) was separated by low speed centrifugation (350 g for 10 minutes). The PRP was diluted 1:1 in buffer A (19 mM phosphate buffer, 0.119 mM NaCl, 3.9 mM KCl, 0.65 mM MgSO$_4$, 0.51 mM CaCl$_2$, 2 mg/ml glucose, 0.2 mg/ml ascorbic acid, $1.6 \times 10^{-4}$ M EDTA and $5.0 \times 10^{-5}$ M pargyline, at pH 7.4) and centrifuged at 1700 g for 20 minutes. The platelet pellet was gently resuspended in buffer A ($10^8$-$10^9$ platelets per ml) and used to measure [$^3$H]5-HT uptake.

Assay of [$^3$H]5-HT Uptake by Human Platelets:

[$^3$H]5-HT uptake assays were carried out as described previously [21]. A standard assay contained 200 μl washed platelets, 50 μl [$^3$H]5-HT and 50 μl buffer A or test drug. The tubes were preincubated at 37° C. for 10 minutes, at which time [$^3$H]5-HT was added (50 nM). After a 2 minute incubation period at 37° C. the reaction was stopped by rapidly cooling the tubes on ice and the mixture was filtered under vacuum on glass fiber filters (GF/C). The filters were washed with ice cold buffer A and the radioactivity was counted in scintillation liquid in a β-counter. Specific uptake was defined as the difference between total [$^3$H]5-HT uptake at 37° C. (triplicate samples) and the uptake measured at 0° C. (duplicate samples).

Measurement of [$^3$H]5-HT Uptake to Rat Brain Synaptosomes:

Rat brain cortex sample was homogenized in 10 volumes of 0.32 M sucrose using a Teflon-glass grinder. The homogenate sample was centrifuged at 1000 g for 10 minutes and the resulting supernatant (S1) containing synaptosomes was used to measure [$^3$H]5-HT uptake.

[$^3$H]5-HT uptake assays were carried out as described previously [21]. A standard assay contained 50 µl synaptosomes, 50 µl [$^3$H]5-HT and 900 µl buffer A (19 mM phosphate buffer, 0.119 mM NaCl, 3.9 mM KCl, 0.65 mM MgSO$_4$, 0.51 mM CaCl$_2$, 2 mg/ml glucose, 0.2 mg/ml ascorbic acid, $1.6 \times 10^{-4}$ M EDTA and $5.0 \times 10^{-5}$ M pargyline, at pH 7.4) or 850 µl buffer A and 50 µl test drug. The tubes were pre-incubated at 37° C. for 10 minutes, at which time [$^3$H]5-HT (50 nM) was added. After a 4 minute incubation period at 37° C. the reaction was stopped by rapidly cooling the tubes on ice and the mixture was filtered under vacuum on glass fiber filters (GF/C). The filters were washed with ice cold buffer A and the radioactivity was counted in scintillation liquid in a β-counter. Specific uptake was defined as the difference between total [$^3$H]5-HT uptake at 37° C. (triplicate samples) and the uptake measured at 0° C. (duplicate samples).

[$^3$H]Ketanserin Binding to Rat Brain Membranes:

[$^3$H]ketanserin binding experiment was performed according to Takao et al. [*Eur. J. Pharmcol.*, 1997, 333, p. 123-8]. Briefly, frozen rat brain cortex was homogenized in 10 volumes of ice cold 0.32 M sucrose using a Teflon-glass homogenizer. The homogenate was centrifuged at 1000 g for 10 minutes at 4° C. and the resulting supernatant was centrifuged at 34000 g for 20 minutes at 4° C. The obtained pellet was homogenized with polytron in 40 volumes 50 mM Tris-HCl buffer pH 7.4 before incubated for 15 min at 37° C. The homogenate was finally centrifuged at 38000 g for 20 min and pellet resuspended in buffer (10 mg protein/ml) and kept at −70° C. until further use.

A standard binding assay contained 200 µl of brain membranes, 100 µl [$^3$H]ketanserin (0.4 nM) and 700 µl buffer or 600 µl buffer and 100 µl test drug. [$^3$H]ketanserin was added to the test tubes after a 3-min preincubation period at 37° C. preceding the 15-minute incubation at 37° C. The homogenates were diluted in 3 ml ice-cold buffer and filtered through Whatman GF/C glass fiber filters pre-incubated in 0.05% polyethyleneimine. Specific binding was defined as the difference between total [$^3$H]ketanserin binding (triplicate samples) and the binding in the presence of 10 µM mianserin (duplicate).

Preparation of Human Platelet Samples for Platelet Aggregation Measurements:

One of the key and essential characteristics of the compounds presented herein is related to inhibition of platelet aggregation by the compounds which do not penetrate the brain and are therefore devoid of CNS effects. It is expected that the potent anti-platelet effects of N-methyl-citalopram would be achieved by in-vivo administration. Presented below is the in-vitro assay, measuring the activity of N-methyl-citalopram as a human platelet aggregation inhibitor after aggregation was induced using serotonin (5-HT).

Fresh human platelet-rich plasma (PRP) was prepared as follows: human platelets were tested for aggregation within 2 hours of withdrawing 10 ml venous blood samples from healthy volunteers, aged between 25-35 years and not taking any drug. Venous blood was withdrawn into citrate Vacutainer tubes (BD #9NC 0.105M) using Vacuette Holdex from Greiner Bio-one (catalogue number 450263) and winged blood collection set (Greiner bio-one #450153). Tubes were mixed gently by inverting them a few times immediately following blood withdrawal. Platelet-rich plasma (PRP) was prepared 45 minutes after blood collection by centrifugation for 10 minutes at 110 g at room temperature in a swinging-bucket centrifuge. The PRP samples obtained were transferred into new tubes and the bloods were centrifuged again at 1900 g for 10 min to yield platelet-poor plasma (PPP). For each PRP sample, the aggregometer was calibrated with the corresponding PPP sample from the same donor.

Measurements of ADP Induced Human Platelet Aggregation:

Platelet aggregation was measured in PRP using an Helena PACKS4 aggregometer (Helena Laboratories, Beaumont, Tex.), following a method described previously [22]. Samples consisting of 198 µl freshly prepared human PRP and 22 µl tested compounds were incubated at 37° C. for 15 minutes in the aggregometer. Stock solutions of citalopram or N-methyl-citalopram were dissolved in calcium-free phosphate-buffered saline (PBS; Biological Industries, Israel, Cat. 02-023-5A) to yield concentrations of 10-fold the final indicated concentration. For control measurements 22 µl of PBS were added.

At the last 30 seconds of incubation 11 µl serotonin were added (final concentration 50 µM serotonin; freshly prepared serotonin solution in PBS) followed 30 seconds later by 25 µl adenosine diphosphate (ADP; final concentration 1.25 µM; freshly prepared ADP solution in PBS) at the end of the incubation. Measurements for platelet aggregation in the aggregometer continued for 5 minutes from the time of ADP addition (time point referred to as "zero").

Determination of [$^3$H]N-Methyl-Citalopram BBB Penetration In-Vivo:

These in-vivo experiments were performed for demonstrating that [$^3$H]N-methyl-citalopram does not penetrate the mouse brain following intraperitoneal injections.

[$^3$H]N-methyl-citalopram was prepared by Vitrax (CA, USA) to a specific radioactivity of 70 Ci/mmol and shown by HPLC to be chemically identical to non-labeled methyl-citalopram. In comparison, [$^3$H]citalopram had a specific radioactivity of 79 Ci/mmol.

Each of the radioactive compounds, [$^3$H]N-methyl-citalopram and [$^3$H] citalopram, was diluted with the same non-radioactive compound so that the dose of the injected compound was 1.5 µg per gram of body weight (weight range 31-43 grams; injection volume range 155-215 µl in saline). The amount of radioactivity (in injected disintegrations per minute, DPM) of the [$^3$H]-labeled compound was 318,000 DPM per gram weight of [$^3$H]N-methyl-citalopram or 174,000 DPM per gram weight of [$^3$H]citalopram. This protocol allowed the amount of injected citalopram dose to be similar to the higher end of the human clinical recommended dosage of 1.5 mg citalopram per kg body weight.

Mice were given 20 mg/kg pentobarbital intraperitoneal injection 10 minutes prior to being perfused with saline for about 2 minutes. The perfusion is required for removing residual blood from the brain tissues and the use of pentobarbital is obligatory due to animal welfare considerations. Saline/heparin perfusion was started at 5, 10, 20 or 40 minutes from the time of intraperitoneal injections of the radioactive compounds. At the end of the perfusion, mice heads were cut off and their dissected brains were washed with ice-cold saline for 30 seconds. The cerebral cortex tissues were dissected according to the Atlas of the Mouse Brain [23] and immediately weighed (weight range: 132-205 mg). The tissues were thereafter homogenized in 10 volumes of distilled water using a Teflon/glass grinder. The radioactivity, expressed as DPM in 500 µl homogenate samples, was counted in a liquid scintillation counter (model 2100TR, Packard, USA) and corrected for DPM using an internal standard.

[$^3$H]Dopamine and [$^3$H]Noradrenaline Uptake by Rat Brain Synaptosomes:

[$^3$H]dopamine and [$^3$H]noradrenaline uptake assays were carried out in synaptosomes from rat brain cortex. After a 10 minutes pre-incubation period at 37° C., [$^3$H]dopamine or [$^3$H]noradrenaline were added to the tubes containing synaptosomes and tested drugs. The reactions were stopped after four minutes by rapid cooling on ice. Specific uptake was defined as the difference between total uptake at 37° C. (triplicate samples) and the uptake measured at 0° C. (duplicate samples). Three separate experiments were performed.

Determination of Bleeding Time in SSRI and Aspirin Treated Mice:

The anti-thrombotic effects of a drug can be evaluated in mice through a bleeding time experiment.

Mice were treated by the tested drugs for two weeks, then anesthetized and placed on a warming pad before a segment of their tail was amputated. The tail was immersed in 0.9% isotonic saline at 37° C., and the time required for the stream of blood to stop was defined as the bleeding time.

Different cuts and drug doses were tested. Control mice were administered either DDW (p.o) or saline (i.p). In some experiments (Nos. 5 and 6), half of the mice were administered DDW and half saline.

Effect of SSRIs in Induced Pulmonary Thromboembolism in Mice:

An experimental model of acute pulmonary thromboembolism was induced in mice by injecting a mixture of collagen (0.5 mg/kg) and epinephrine (0.5 mg/kg). Mice treated chronically with aspirin (70 mg/kg), citalopram (10 mg/kg), NMC (10 mg/kg) or saline for two weeks were injected via vein tail with collagen-epinephrine solution. The injection was followed by a massive activation of circulating platelets and the widespread formation of platelet thrombi in the microcirculation of the lungs leading to disseminated pulmonary microembolism and paralysis of the animal.

Toxicology Preliminary Experiment:

ICR mice were administered (i.p.) once a day high doses of citalopram or NMC (2 or 3 mice per dose). These mice were then observed for 1 hour. The doses were up to 10-fold higher than the highest doses used in the bleeding time or the pulmonary thromboembolism experiments presented hereinabove.

EXPERIMENTAL RESULTS

In Vitro Studies

Preparation of N-methyl-citalopram:

N-methyl-citalopram (NMC, 1.8 grams) was synthesized via methylation of citalopram, using methyl iodide. The purity of NMC and the absence of citalopram were verified by HPLC.

Assay of [$^3$H]Citalopram Binding to Human Platelets:

The affinity of N-methyl-citalopram (NMC) to the 5-HT transported (5-HTT) in human platelets was compared to the affinity of citalopram, as presented hereinabove.

FIG. 1 presents comparative plots, showing the inhibition of the binding of [$^3$H]citalopram to the human platelet membranes serotonin transporter by NMC or citalopram as a function of the concentration of the competitive inhibitor. The assay was carried out by competition binding experiments carried out in human platelet membranes, using [$^3$H]citalopram as the labeled ligand.

Table 2 present the [$^3$H]citalopram binding and [$^3$H]5-HT uptake inhibition constants in rat brain and human platelets. In Table 2, values represent the means±S.E.M. obtained from 2-3 independent experiments each conducted in triplicate. See Methods for further details.

TABLE 2

| | Ki (nM) rat brain | | Ki (nM) human platelets | |
|---|---|---|---|---|
| | [$^3$H]citalopram binding | [$^3$H]5-HT uptake | [$^3$H]citalopram binding | [$^3$H]5-HT uptake |
| Citalopram | 3 ± 1 | 4.5 ± 0.7 | 6.32 ± 1.10 | 4.3 ± 0.9 |
| NMC | 53 ± 15[a] | 44 ± 6.6[b] | 62 ± 8.3[c] | 52.0 ± 15[d] |

A significant difference of Ki values was observed in rat brain:
[a] p = 0.029,
[b] p = 0.001 versus citalopram as well as in platelets
[c] p < 0.0001,
[d] p = 0.193 (n = 2) versus citalopram.

As can be seen in FIG. 1 and Table 2, N-methyl-citalopram recognized the human platelet 5-HTT with lower (about 10-fold) affinity as compared to that of to citalopram (Ki values of 62.00±8.3 nM and 6.32±1.10 nM for NMC and citalopram, respectively).

FIG. 2 presents comparative plots, showing the inhibition of serotonin uptake in intact freshly prepared human platelets effected by the presence of NMC or citalopram, expressed in percent of inhibition of the uptake of [$^3$H]serotonin as a function of the concentration of the tested compounds.

As can be seen in FIG. 2 and Table 2, NMC was shown to inhibit [$^3$H]5-HT uptake in freshly isolated human platelets with an inhibition constant (Ki) value of 52.0±15 nM, compared with 4.3±0.9 nM as determined for citalopram.

The capacity of NMC to compete for [$^3$H]citalopram binding and to inhibit [$^3$H]5-HT uptake in human platelets indicate that NMC is a potent anti-platelet agent.

Assay of [$^3$H]Citalopram Binding and [$^3$H]5-HT Uptake in Rat Brain:

FIG. 3 presents comparative plots, showing the inhibition of the binding of [$^3$H]citalopram to the rat brain membranes serotonin transporter (5-HTT) by N-methyl-citalopram (NMC) or citalopram as a function of the concentration of the competitive inhibitor. The Ki values in the 5-HTT binding experiments in rat brain membranes, were 53±15 nM for NMC and 3±1 nM for citalopram.

FIG. 4 presents comparative plots, showing the inhibition of [$^3$H]serotonin uptake in freshly prepared rat brain synaptosomes effected by the presence of the tested compounds, NMC and citalopram, expressed in percent of inhibition of the uptake of [$^3$H]serotonin. The Ki values of the [$^3$H]5-HT uptake experiments in rat brain synaptosomes, were 44±6.6 nM for NMC and 4.5±0.7 nM for citalopram.

As can be seen in FIGS. 3 and 4, NMC exhibited about the same activity in rats as observed in the assay for human platelets (FIGS. 1 and 2).

Even if small amounts of NMC do penetrate the BBB during chronic treatment, its biological CNS activity is expected to be about 10-fold less potent for the CNS 5-HTT compared with citalopram, as shown by its reduced affinity in competing for [³H]citalopram binding (almost 20-fold less) or to inhibit [³H]5-HT uptake (8-fold less) in the rat brain, as compared with citalopram (see, FIGS. 3 and 4).

Measurements of ADP Induced Human Platelet Aggregation:

Serotonin, which is known to increase the platelet aggregation effects of the classical platelet agonists ADP [24, 25], collagen [26] or adrenaline [27], was used in these experiments together with ADP to induce platelet aggregation. This was employed to show that both tested compounds, citalopram and N-methyl-citalopram (100 µM), can strongly inhibit the aggregation of human platelets induced by 1.25 µM ADP in the presence of 50 µM serotonin.

Platelet-rich plasma (PRP) samples were pre-incubated with the tested compounds or PBS control as described hereinabove. FIG. 5 presents comparative plots of the measurement of platelet aggregation as recorded for a sample from a healthy donor, showing the percent inhibition of human platelet aggregation effected by citalopram (plot denoted "Channel 4" and colored in brown), by N-methyl-citalopram (plot denoted "Channel 3" and colored in blue), and by the control PBS (plot denoted "Channel 2" and colored in red).

FIG. 6 presents a repeat of the experiment presented in FIG. 5 as measured for a sample taken from the same healthy donor, showing the percent inhibition of human platelet aggregation effected by citalopram (plot denoted "Channel 3" and colored in blue), by N-methyl-citalopram (plot denoted "Channel 2" and colored in red), and by the control PBS (plot denoted "Channel 1" and colored in green).

As can be seen in both FIGS. 5 and 6, the addition of ADP initiates platelet aggregation within about 20 seconds. For the PRP samples pre-incubated for 15 minutes with PBS as control, platelets aggregation has reached a value of 85.1% or 91.8% of the maximal possible aggregation, for measurements presented in FIGS. 5 and 6 respectively, during the period of 5 minutes observation by the aggregometer. For PRP samples pre-incubated with citalopram (final concentration 100 µM) the aggregation had reached a value representing only 23.1% and 28.7%, for measurements presented in FIGS. 5 and 6, respectively, of the maximum possible aggregation. For PRP samples pre-incubated with N-methyl-citalopram (final concentration 100 µM) the aggregation has reached a value representing only 20.2% and 22.9%, for measurements presented in FIGS. 5 and 6, respectively, of the maximum possible aggregation.

Both tested compounds exhibited strong inhibition of platelet aggregation.

Noted herein is that for both the tested compounds and the control PBS, there was a very similar early phase of platelet aggregation, which took place between about 40 seconds to 75 seconds following the addition of ADP. However, while for the PBS control there was a second phase of platelet aggregation, taking place from about 75 seconds to 300 seconds following ADP addition, this second phase was entirely absent in the PRP samples which were pre-incubated with citalopram or N-methyl-citalopram.

In particular, it can be seen that the tested compounds block the second (slower) phase of platelet aggregation. Furthermore, the data represent inhibition in-vitro, however they were obtained with freshly isolated human platelets of a healthy donor, and are the closest possible demonstration in lieu of permission to give the tested compounds to human volunteers. Yet, considering that one of the tested compounds, citalopram, has been shown (among other SSRI drugs) to substantially reduce the risk of ischemic heart disease and MI in patients who take it chronically as discussed hereinabove, it is stated herein that N-methyl-citalopram would be capable of inducing the same beneficial effect in-vivo but without penetrating the brain, and therefore not having undesired CNS effects typical for SSRI drugs.

[³]Dopamine and [³H]Noradrenaline Uptake by Rat Brain Synaptosomes:

FIGS. 7A-B present a plot of [³H]dopamine uptake (FIG. 7A) and [³H]noradrenaline uptake (FIG. 7B) into rat brain synaptosomes as a function of the concentration of a drug, comparing the inhibitory effect of citalopram, NMC and mazindol.

As can be seen in FIGS. 7A-B, mazindol, an inhibitor of dopamine and noradrenaline uptake, inhibited [³H]dopamine uptake by 50% at 45 nM. At this concentration citalopram did not inhibit the uptake of dopamine while NMC exhibited less than 10% inhibition. The uptake of [³H]noradrenaline was inhibited by 50% at 8.5 nM mazindol whereas at this concentration citalopram did not have any effect and NMC inhibited less than 20% of the uptake.

[³H]Ketanserin Binding by Rat Brain Membranes:

The affinity of N-methyl-citalopram to rat brain membranes serotonin 5-HT$_{2A}$ receptors was evaluated in [³H]ketanserin binding assay. IC$_{50}$ of the 5-HT$_{2A}$ antagonist mianserin was 3.3 nM while up to 10 µM of either citalopram or NMC did not inhibit [³H]ketanserin (data not shown).

EXPERIMENTAL RESULTS

In Vivo Studies

Determination of [3 µl]N-Methyl-Citalopram BBB Penetration In-Vivo:

The experiment was designed to show that N-methyl-citalopram does not penetrate the mouse brain following intraperitoneal injection, as opposed to the uncharged counterpart, citalopram, using [³H]-labeled samples thereof. The detected disintegrations per minute (DPM) values at the different times after injection of either [³H]N-methyl-citalopram or [³H]citalopram are shown in FIG. 8.

FIG. 8 presents comparative plots of the accumulation of [³H] disintegration events per minute (DPM) in the cerebral cortex samples of mice after the indicated times following the intraperitoneal injection of either [³H]N-methyl-citalopram (marked in red circles) and [³H]citalopram (marked in black rectangles). The values represent the mean+/–standard deviations (SD) for 3 mice for each compound, and for a single mouse the time-point of 40 minutes. SD values for the measurements in mice injected with N-methyl-citalopram were too small to be shown on this scale.

As can be seen in FIG. 8, [³H]citalopram readily entered the brain shortly after its injection at the clinically relevant dose of 1.5 mg per kg body weight, reaching levels of about 3350 DPM per 500 µl cerebral cortex homogenate sample at 40 minutes, corresponding to about 13,400 DPM for the entire cerebral cortex.

In sharp contrast, only very low amounts of radioactivity were detected in the brain homogenate samples of mice following injections of a similar dose (1.5 mg per kg body weight) of [³H]N-methyl-citalopram, as can be clearly seen in FIG. 8. The radioactivity levels, expressed in DPM, in these brain homogenate samples were about 30-fold lower compared with the radioactivity levels in mice injected with [³H]citalopram. These DPM counts, ranging from 50 DPM at 5 minutes to 110 DPM at 40 minutes were only slightly above the background radioactivity of about 20 DPM.

Taking into consideration that the amount of radioactivity of injected [³H]N-methyl-citalopram was almost twice compared with that of [³H]citalopram, these data represent more than 50-fold less brain penetration for [³H]N-methyl-citalopram compared with brain penetration for [³H]citalopram.

These results clearly show that [³H]N-methyl-citalopram does not, or only minimally penetrate the mouse brain following intraperitoneal injection. Based on these results, it is estimated that the brain penetration of N-methyl-citalopram following its intraperitoneal injection is about 50-fold less than that of citalopram. It is well established that compounds behave similarly with respect to penetration of the human or mouse brain following their administration to a peripheral organ. Hence, a compound that does not or only minimally enter the mouse brain will show the same pattern for penetrating the human brain.

Determination of Bleeding Time in SSRI and Aspirin Treated Mice:

The working assumption in these experiments was that mice treated with aspirin or SSRIs are expected to be protected against the induced pulmonary thromboembolism.

Tables 3, 4 and 5 present the results of the bleeding tests as described hereinabove.

Table 3 presents data collected from chronically medicated mice having their tail bleeding time measured after amputation of 3 mm from their tail.

TABLE 5

| | Experiment No. | Mice used | Dose (mg/kg) | N | Mean bleeding time (sec.) | standard deviation |
|---|---|---|---|---|---|---|
| control | 1 | CJ57/black | DDW | 10 | 174 | 165 |
| aspirin | 1 | CJ57/black | 40 | 5 | 233 | 222 |
| citalopram | 1 | CJ57/black | 1.5 | 5 | 105 | 32 |
| NMC | 1 | CJ57/black | 1.5 | 5 | 210 | 218 |

As can be seen in Tables 3-5, chronic treatment of mice with NMC resulted in a comparable effect on the increased bleeding as observed with the other drugs used in the experiment. When all experiments were combined, no significant differences were noted as compared to control groups. Furthermore, notable standard variation values were obtained in all groups representing a high variability of bleeding time between individual mice in all groups. There is however an indication that low doses of citalopram or NMC (1.5 mg/kg/day) were more effective than the higher doses (2 or 4.5

TABLE 3

| | Experiment No. | Mice used | Dose (mg/kg) | Route of administration | N | Mean bleeding time (sec.) | standard deviation | Mean (n = 4) |
|---|---|---|---|---|---|---|---|---|
| Control | 1 | CJ57/black | DDW | p.o | 4 | 97 | 45 | 179 |
| | 2 | CJ57/black | DDW | p.o | 12 | 277 | 252 | |
| | 3 | CJ57/black | DDW | p.o | 15 | 150 | 187 | |
| | 4 | CJ57/black | DDW | p.o | 16 | 157 | 193 | |
| | 5 | ICR | DDW or saline | p.o/i.p | 15 | 126 | 134 | |
| Aspirin | 2 | CJ57/black | 40 | p.o | 12 | 389 | 228 | 288 |
| | 3 | CJ57/black | 40 | p.o | 14 | 230 | 225 | |
| | 4 | CJ57/black | 70 | p.o | 13 | 394 | 257 | |
| | 5 | ICR | 70 | p.o | 14 | 145 | 186 | |
| Citalopram | 1 | CJ57/black | 1.5 | p.o | 4 | 472 | 255 | 171 |
| | 2 | CJ57/black | 1.5 | p.o | 12 | 232 | 226 | |
| | 3 | CJ57/black | 2 | p.o | 14 | 179 | 221 | |
| | 4 | CJ57/black | 4.5 | p.o | 14 | 115 | 149 | |
| | 5 | ICR | 10 | i.p | 12 | 66 | 23 | |
| NMC | 1 | CJ57/black | 1.5 | p.o | 5 | 414 | 265 | 191 |
| | 2 | CJ57/black | 1.5 | p.o | 11 | 337 | 259 | |
| | 3 | CJ57/black | 2 | p.o | 15 | 150 | 187 | |
| | 4 | CJ57/black | 4.5 | p.o | 15 | 108 | 78 | |
| | 5 | ICR | 10 | i.p | 13 | 124 | 144 | |

Table 4 presents data collected from chronically medicated mice having their tail bleeding time measured after amputation of 4 mm from their tail.

TABLE 4

| | Experiment No. | Mice used | Dose (mg/kg) | Route of administration | N | Mean bleeding time (sec.) | standard deviation |
|---|---|---|---|---|---|---|---|
| control | 6 | ICR | DDW or saline | p.o/i.p | 23 | 218 | 194 |
| aspirin | 6 | ICR | 40 | p.o | 19 | 221 | 219 |
| citalopram | 6 | ICR | 1.5 | i.p | 27 | 214 | 202 |
| NMC | 6 | ICR | 1.5 | i.p | 27 | 225 | 215 |

Table 5 presents data collected from chronically medicated mice (p.o. administration mode) having their tail bleeding time measured after amputation of a segment corresponding to the area where tail diameter is 2 mm at 1.5 mm depth into a tail restrainer.

mg/kg/day). It is also noted that the oral (p.o.) administration of these drugs is more effective than i.p. injections in prolonging bleeding times.

Effect of SSRIs in Induced Pulmonary Thromboembolism in Mice:

Table 6 present percentage of mice who died or were paralyzed (loss of righting reflex for more than 30 seconds) after injection of collagen-epinephrine into tail vein. In Table 6, $^a$p=0.016 and $^b$p=0.05 according to Mann-Whitney test versus control group.

As can be seen in Table 6, mice treated with aspirin were significantly less prone to die or to be paralyzed after the injection of collagen-epinephrine mixture into tail vein. NMC administered chronically to mice led also to a significant decrease in death or paralysis after the mixture injection.

Surprisingly, citalopram did not cause a significant improvement compared to control group.

TABLE 6

|  | Experiment No. | Number of mice who died | % death | Mean % death ± S.E.M |
|---|---|---|---|---|
| Control | 1 | 7/10 | 70 |  |
|  | 2 | 6/7 | 86 | 72 ± 2 |
|  | 3 | 8/13 | 61 |  |
| Aspirin | 1 | 5/10 | 50 |  |
|  | 2 | 5/12 | 42 | 40$^a$ ± 7 |
|  | 3 | 3/11 | 27 |  |
| Citalopram | 1 | 7/9 | 78 |  |
|  | 2 | 8/13 | 61 | 70 ± 5 |
|  | 3 | 7/10 | 70 |  |
| NMC | 1 | 6/8 | 75 |  |
|  | 2 | 4/13 | 31 | 50$^b$ ± 10 |
|  | 3 | 6/14 | 43 |  |

Toxicology Preliminary Experiment:

Tables 7 and 8 present toxicology test results, showing mice reactions following i.p injections of citalopram (Table 7) or NMC (Table 8) observed over a period of three consecutive days.

TABLE 7

| Dose injected | Mouse number | Mice behavior following citalopram injections | | |
|---|---|---|---|---|
|  |  | day 1 | day 2 | day 3 |
| 30 mg/day | 1 | normal | slower movements and reactions | slower movements and reactions |
|  | 2 | normal | slower movements and reactions | slower movements and reactions |
| 50 mg/day | 1 | look quiet, mobility reduction | look quiet, mobility reduction | looks quiet, mobility reduction |
|  | 2 | look quiet, mobility reduction | look quiet, mobility reduction | looks quiet, mobility reduction |
| 100 mg/day | 1 | slower movements and reactions | slower movements and reactions, looks weak and convulsions (weight reduction) | looks weak, convulsions then recovered |
|  | 2 | slower movements and reactions, apathetic | Weak and somnolent (weigh reduction) | looks weak |

TABLE 8

| Dose injected | Mouse number | Mice behavior following NMC injections | | |
|---|---|---|---|---|
|  |  | day 1 | day 2 | day 3 |
| 30 mg/day | 1 | normal | normal (weight reduction) | normal |
|  | 2 | normal | normal (weight reduction) | normal |
| 50 mg/day | 1 | normal | normal | laid aside then recovered |
|  | 2 | look weak and lies aside | difficulty to move posterior legs | laid aside then recovered |

TABLE 8-continued

| Dose injected | Mouse number | Mice behavior following NMC injections | | |
|---|---|---|---|---|
|  |  | day 1 | day 2 | day 3 |
| 100 mg/day | 1 | laid aside then recovered | laid aside then recovered | difficulty to move posterior legs, fast breathing, laid aside then recovered |
|  | 2 | Convulsions and death 10 min after injection |  |  |
|  | 3 |  | laid aside then recovered | laid aside then recovered |

As can be seen in Tables 7 and 8, mice overdosed with NMC exhibited adverse effects, yet, at less than 50 mg/kg NMC is not lethal to mice. In doses above 50 mg/kg of NMC can be toxic and a dose of 100 mg/kg can be lethal.

The results presented above clearly show that NMC is a promising anti-platelet drug, which does not cross the BBB and penetrate the brain, and is therefore devoid of the adverse CNS influent of citalopram. These observations indicate that similar quaternary-nitrogen SRI compounds are likely to maintain their capacity for recognizing the human platelet 5-HTT and inhibiting its activity similarly to their parent compounds in which the nitrogen atom is tertiary and which therefore do penetrate the BBB.

The in vivo results clearly demonstrated that NMC does not penetrate the BBB while exerting peripheral anti-clotting effect as high as other known drugs by protecting NMC-treated mice from acute pulmonary thromboembolism; and preliminary in vivo toxicology studies showed that NMC is none-toxic at efficacious doses.

Therefore, NMC and similar quaternary SRI compounds have a clinical potential as anti-platelet agents (decreasing platelet aggregation) while being devoid of the undesired CNS effects of currently marketed SRI drugs, such as flattened emotions, reduced libido, and aggressiveness sometimes associated with current SRI compounds.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited in the Text

1. Ho, W. K., G. J. Hankey, and J. W. Eikelboom, *Prevention of coronary heart disease with aspirin and clopidogrel: efficacy, safety, costs and cost-effectiveness.* Expert Opin Pharmacother, 2004. 5(3): p. 493-503.
2. Manolis, A. S., et al., *Aspirin and clopidogrel: a sweeping combination in cardiology.* Curr Med Chem Cardiovasc Hematol Agents, 2005. 3(3): p. 203-19.
3. Nobles-James, C., E. A. James, and J. R. Sowers, *Prevention of cardiovascular complications of diabetes mellitus by aspirin.* Cardiovasc Drug Rev, 2004. 22(3): p. 215-26.
4. Schumacher, W. A., et al., *Biomarker optimization to track the antithrombotic and hemostatic effects of clopidogrel in rats.* J Pharmacol Exp Ther, 2007.
5. McCaffery, J. M., et al., *Common genetic vulnerability to depressive symptoms and coronary artery disease: a review and development of candidate genes related to inflammation and serotonin.* Psychosom Med, 2006. 68(2): p. 187-200.
6. Paraskevaidis, I., et al., *Selective serotonin re-uptake inhibitors for the treatment of depression in coronary artery disease and chronic heart failure: evidence for pleiotropic effects.* Cardiovasc Hematol Agents Med Chem, 2006. 4(4): p. 361-7.
7. Sauer, W. H., J. A. Berlin, and S. E. Kimmel, *Selective serotonin reuptake inhibitors and myocardial infarction.* Circulation, 2001. 104(16): p. 1894-8.
8. Sauer, W. H., J. A. Berlin, and S. E. Kimmel, *Effect of antidepressants and their relative affinity for the serotonin transporter on the risk of myocardial infarction.* Circulation, 2003. 108(1): p. 32-6.
9. Walther, D. J., et al., *Serotonylation of small GTPases is a signal transduction pathway that triggers platelet alpha-granule release.* Cell, 2003. 115(7): p. 851-62.
10. Serebruany, V. L., et al., *Platelet/endothelial biomarkers in depressed patients treated with the selective serotonin reuptake inhibitor sertraline after acute coronary events: the Sertraline AntiDepressant Heart Attack Randomized Trial (SADHART) Platelet Substudy.* Circulation, 2003. 108(8): p. 939-44.
11. Weyrich, A. S., S. M. Prescott, and G. A. Zimmerman, *Platelets, endothelial cells, inflammatory chemokines, and restenosis: complex signaling in the vascular play book.* Circulation, 2002. 106(12): p. 1433-5.
12. Kawut, S. M., et al., *Selective serotonin reuptake inhibitor use and outcomes in pulmonary arterial hypertension.* Pulm Pharmacol Ther, 2006. 19(5): p. 370-4.
13. Fujita, M., et al., *Sarpogrelate treatment reduces restenosis after coronary stenting.* Am Heart J, 2003. 145(3): p. E16.
14. Slaughter, J. R., et al., *Clinical outcomes following a trial of sertraline in rheumatoid arthritis.* Psychosomatics, 2002. 43(1): p. 36-41.
15. Moore, M. C., et al., *Portal infusion of a selective serotonin reuptake inhibitor enhances hepatic glucose disposal in conscious dogs.* Am J Physiol Endocrinol Metab, 2004. 287(6): p. E1057-63.
16. Hofstetter, H. H., et al., *Absence of reuptake of serotonin influences susceptibility to clinical autoimmune disease and neuroantigen-specific interferon-gamma production in mouse EAE.* Clin Exp Immunol, 2005. 142(1): p. 39-44.
17. Sidel'nikov Iu, N. and G. A. Sivoraksha, [*The participation of histamine and serotonin in the genesis of acute kidney failure in patients with hemorrhagic fever with renal syndrome*]. Urol Nefrol (Mosk), 1990(4): p. 46-8.
18. Mikocka-Walus, A. A., et al., *Antidepressants and inflammatory bowel disease: a systematic review.* Clin Pract Epidemol Ment Health, 2006. 2(1): p. 24.
19. Guignabert, C., et al., *Transgenic mice overexpressing the 5-hydroxytryptamine transporter gene in smooth muscle develop pulmonary hypertension.* Circ Res, 2006. 98(10): p. 1323-30.
20. Plenge, P. and E. T. Mellerup, [$3H$]*citalopram binding to brain and platelet membranes of human and rat.* J Neurochem, 1991. 56(1): p. 248-52.
21. Rehavi, M., et al., *2-nitroimipramine: a selective irreversible inhibitor of [$3H$] serotonin uptake and [$3H$] imipramine binding in platelets.* Biochem Biophys Res Commun, 1981. 99(3): p. 954-9.
22. Awabdy, D., L. J. Bryan-Lluka, and J. C. Wanstall, *5-Hydroxytryptamine and platelets: uptake and aggregation in hypoxic pulmonary hypertensive rats.* Eur Pharmacol, 2003. 459(1): p. 1-7.
23. Sidman, R. L. and E. T. Pierce, *Atlas of the Mouse Brain and Spinal Cord.* 1971.
24. Smith, G. M., *Involvement of 5-hydroxytryptamine in platelet aggregation in vivo in rats and guinea pigs.* Thromb Haemost, 1989. 61(3): p. 463-7.
25. Vanags, D. M., et al., *Potentiation of ADP-induced aggregation in human platelet-rich plasma by 5-hydroxytryptamine and adrenaline.* Br J Pharmacol, 1992. 106(4): p. 917-23.
26. Takano, S., *Role of 5-hydroxytryptamine in platelet thrombus formation and mechanisms of inhibition of thrombus formation by 5-hydroxytryptamine2A antagonists in rabbits.* Arch Int Pharmacodyn Ther, 1995. 330(3): p. 297-308.
27. Alarayyed, N. A., et al., *The potentiation of adrenaline-induced in vitro platelet aggregation by ADP, collagen and serotonin and its inhibition by naftopidil and doxazocin in normal human subjects.* Br J Clin Pharmacol, 1995. 39(4): p. 369-74.

What is claimed is:

1. A method of treating a disease or disorder in which reducing or preventing platelet aggregation and/or platelet-endothelial interactions is beneficial, the method comprising administering to a subject in need thereof a therapeutically effective amount of a serotonin reuptake inhibitor (SRI) compound which comprises citalopram modified so as to comprise at least one positively charged group, said at least one positively charged group being a quaternary ammonium group, wherein said quaternary ammonium group has the formula:

—(NR$_1$R$_2$R$_3$)$^+$Z$^-$ wherein:
Z is an organic or inorganic anion;
R$_1$ and R$_2$ are each methyl; and
R$_3$ is alkyl having from 1 to 4 carbon atoms.

2. The method of claim 1, further comprising administering to the subject a therapeutically effective amount of an additional therapeutically active agent.

3. The method of claim 1, wherein R$_3$ is methyl.

4. The method of claim 1, wherein said SRI compound is substantially incapable of modulating a serotonin level in the CNS of said subject.

5. The method of claim 4, wherein said reducing or preventing platelet aggregation and/or platelet-endothelial interactions is effected while substantially maintaining a level and/or activity of central serotonin, thereby avoiding CNS-related effects.

6. The method of claim 1, wherein said disease or disorder is selected from the group consisting of a cardiovascular disease or disorder, a cerebrovascular disease or disorder, ischemic heart disease (IHD), myocardial infarction (MI), cerebral stroke, pulmonary embolism, type-2 diabetes-associated vascular abnormalities, pulmonary arterial hypertension, peripheral arterial occlusive disease, acute coronary syndrome, coronary artery disease (CAD) and coronary artery bypassing post-grafting.

7. The method of claim 2, wherein said additional therapeutically active agent is an anti-platelet agent.

* * * * *